(12) United States Patent
Hikosaka

(10) Patent No.: US 10,945,698 B2
(45) Date of Patent: Mar. 16, 2021

(54) RADIATION IMAGING APPARATUS, RADIATION IMAGING SYSTEM, RADIATION IMAGING METHOD, AND STORAGE MEDIUM

(71) Applicant: CANON KABUSHIKI KAISHA, Tokyo (JP)

(72) Inventor: Manami Hikosaka, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 320 days.

(21) Appl. No.: 15/635,976

(22) Filed: Jun. 28, 2017

(65) Prior Publication Data

US 2018/0008226 A1    Jan. 11, 2018

(30) Foreign Application Priority Data

Jul. 5, 2016   (JP) .............................. JP2016-132997

(51) Int. Cl.
  *A61B 6/00*   (2006.01)
(52) U.S. Cl.
  CPC .............. *A61B 6/585* (2013.01); *A61B 6/545* (2013.01)
(58) Field of Classification Search
  CPC ....................................................... A61B 6/585
  See application file for complete search history.

(56) References Cited

U.S. PATENT DOCUMENTS

| 4,903,705 | A | * | 2/1990 | Imamura | ................ | A61B 6/481 |
| | | | | | | 348/E5.089 |
| 5,569,907 | A | * | 10/1996 | Meunier | .............. | H04N 3/1593 |
| | | | | | | 250/208.1 |
| 5,807,256 | A | * | 9/1998 | Taguchi | ................ | G06F 19/321 |
| | | | | | | 600/300 |
| 6,163,339 | A | * | 12/2000 | Meunier | .............. | H04N 3/1593 |
| | | | | | | 250/208.1 |
| 6,217,188 | B1 | * | 4/2001 | Wainwright | ......... | A41D 27/085 |
| | | | | | | 362/103 |

(Continued)

FOREIGN PATENT DOCUMENTS

| CN | 102274035 A | 12/2011 |
| CN | 102688051 A | 9/2012 |

(Continued)

OTHER PUBLICATIONS

Notice of Reasons for Refusal issued by the Japan Patent Office dated Jul. 9, 2020 in corresponding JP Patent Application No. 2016-132997, with English translation.

(Continued)

*Primary Examiner* — David P Porta
*Assistant Examiner* — Djura Malevic
(74) *Attorney, Agent, or Firm* — Carter, DeLuca & Farrell LLP

(57) ABSTRACT

Provided is a radiation imaging apparatus, including: a radiation detector configured to detect radiation; a first detector designation unit configured to designate a first radiation detector; a second detector designation unit configured to designate a second radiation detector registered in the radiation imaging apparatus in advance; and an information control unit configured to associate setting information on the second radiation detector with the first radiation detector after the first radiation detector and the second radiation detector are designated.

15 Claims, 21 Drawing Sheets

(56) References Cited

U.S. PATENT DOCUMENTS

| | | | | |
|---|---|---|---|---|
| 6,859,521 B2* | 2/2005 | Spahn | A61B 6/08 | 378/117 |
| 7,120,229 B2* | 10/2006 | Takasawa | A61B 6/00 | 378/98.2 |
| 7,324,679 B2* | 1/2008 | Moriyama | G03B 42/00 | 382/132 |
| 7,751,529 B2* | 7/2010 | Ohara | A61B 6/00 | 378/116 |
| 7,764,765 B2* | 7/2010 | Ohta | A61B 6/4233 | 250/370.09 |
| 7,772,560 B2* | 8/2010 | Ohta | A61B 6/00 | 250/370.09 |
| 8,077,828 B2* | 12/2011 | Aoyama | A61B 6/465 | 378/108 |
| 8,165,372 B2* | 4/2012 | Ishikawa | A61B 5/0095 | 128/922 |
| 8,194,823 B2* | 6/2012 | Ohta | A61B 6/4233 | 250/370.09 |
| 8,295,439 B2* | 10/2012 | Yonekawa | A61B 6/00 | 378/115 |
| 8,618,491 B2* | 12/2013 | Shimizukawa | A61B 6/4233 | 250/370.09 |
| 8,654,925 B2* | 2/2014 | Nishino | A61B 6/4405 | 378/115 |
| 8,727,619 B2* | 5/2014 | Yamamichi | A61B 6/4494 | 378/207 |
| 8,786,873 B2* | 7/2014 | Sabol | G06Q 50/22 | 358/1.15 |
| 8,821,376 B2* | 9/2014 | Tolkowsky | A61B 1/0052 | 600/101 |
| 9,131,905 B2* | 9/2015 | Abe | A61B 6/00 | |
| 9,134,436 B2* | 9/2015 | Kwak | A61B 6/548 | |
| 9,192,350 B2* | 11/2015 | Hiroike | H05G 1/08 | |
| 9,195,899 B2* | 11/2015 | Topfer | G06K 9/38 | |
| 9,198,270 B2* | 11/2015 | Chicchetti | H05G 1/08 | |
| 9,402,592 B2* | 8/2016 | Garcia | A61B 6/4283 | |
| 9,405,183 B2* | 8/2016 | Ando | A61B 6/4266 | |
| 9,538,978 B2* | 1/2017 | Makino | G16H 40/63 | |
| 9,655,575 B2* | 5/2017 | Park | A61B 6/4233 | |
| 9,814,435 B2* | 11/2017 | Kim | A61B 6/469 | |
| 9,826,948 B2* | 11/2017 | Lee | A61B 6/42 | |
| 10,039,509 B2* | 8/2018 | Okusu | A61B 6/4208 | |
| 10,045,751 B2* | 8/2018 | Okusu | A61B 6/563 | |
| 2002/0049378 A1* | 4/2002 | Grzeszczuk | A61B 90/36 | 600/427 |
| 2003/0021455 A1* | 1/2003 | Dixon | A61B 6/4233 | 382/132 |
| 2004/0066900 A1* | 4/2004 | Motoki | G16H 40/63 | 378/116 |
| 2004/0138548 A1 | 7/2004 | Strommer et al. | | |
| 2005/0033149 A1* | 2/2005 | Strommer | A61B 5/0555 | 600/407 |
| 2005/0152592 A1* | 7/2005 | Kasai | G06T 7/0012 | 382/132 |
| 2005/0169425 A1* | 8/2005 | Takasawa | A61B 6/00 | 378/97 |
| 2007/0165783 A1* | 7/2007 | Abu Tabanjeh | A61B 6/00 | 378/116 |
| 2008/0049901 A1* | 2/2008 | Tamakoshi | A61B 6/00 | 378/98.2 |
| 2009/0022276 A1* | 1/2009 | Ohara | A61B 6/00 | 378/101 |
| 2009/0032745 A1* | 2/2009 | Kito | A61B 6/00 | 250/582 |
| 2009/0130983 A1* | 5/2009 | Venturino | A61B 6/00 | 455/66.1 |
| 2009/0196398 A1* | 8/2009 | Ohara | A61B 6/00 | 378/98.5 |
| 2010/0041949 A1* | 2/2010 | Tolkowsky | A61B 1/0052 | 600/109 |
| 2010/0054417 A1* | 3/2010 | Nishino | A61B 6/00 | 378/98.8 |
| 2010/0239150 A1* | 9/2010 | Ishikawa | A61B 5/0095 | 382/131 |
| 2011/0051896 A1* | 3/2011 | Abe | A61B 6/00 | 378/98.8 |
| 2011/0274251 A1* | 11/2011 | Omernick | G01T 7/00 | 378/98.8 |
| 2012/0195407 A1* | 8/2012 | Nenoki | A61B 6/4283 | 378/98.5 |
| 2012/0207278 A1* | 8/2012 | Yonekawa | A61B 6/4233 | 378/98.5 |
| 2013/0064351 A1* | 3/2013 | Urbon | A61B 6/4283 | 378/98.5 |
| 2013/0156267 A1* | 6/2013 | Muraoka | A61B 6/5217 | 382/103 |
| 2014/0010353 A1* | 1/2014 | Lalena | A61B 6/566 | 378/98 |
| 2014/0151563 A1* | 6/2014 | Rousso | G01T 1/161 | 250/362 |
| 2014/0254760 A1* | 9/2014 | Hiroike | A61B 6/4233 | 378/62 |
| 2015/0131782 A1* | 5/2015 | Park | A61B 6/4405 | 378/62 |
| 2019/0231299 A1* | 8/2019 | Lalena | A61B 6/563 | |

FOREIGN PATENT DOCUMENTS

| | | |
|---|---|---|
| CN | 102727226 A | 10/2012 |
| CN | 104027123 A | 9/2014 |
| CN | 105919611 A | 9/2016 |
| JP | 2003210450 A | 7/2003 |
| JP | 2013-39198 A | 2/2013 |
| JP | 2014079570 A | 5/2014 |

OTHER PUBLICATIONS

Chinese Office Action dated Dec. 14, 2020, for Corresponding Chinese Application No. 201710536936.X.

* cited by examiner

FIG. 7

INTRODUCED DETECTOR:

| | MODEL | SERIAL NUMBER | DETECTOR TYPE |
|---|---|---|---|
| ☐ | CXDI710C-Wireless | 2800FF09 | 70C |
| ☑ | CXDI50G | 10000010 | 50G |
| ☐ | CXDI70C-Wireless | 1800FF04 | 70C |

REMOVED DETECTOR:

| | DETECTOR NAME | SERIAL NUMBER | DETECTOR TYPE | SETTING INFORMATION |
|---|---|---|---|---|
| ☑ | CXDI50G-01 | 10000000 | 50G | WS-50G , WS-50G-Stand |
| ☐ | CXDI50G-02 | 10000001 | 50G | WS-50G , WS-50G-Table |
| ☒ | 70C-Wireless | 1800FF01 | 70C | WS-70CGr. |
| ☒ | 710C-Wireless | 2800FF03 | 70C | WS-710C-2, WS-70CGr. |

[REPLACE] [CANCEL]

FIG. 18

INTRODUCED DETECTOR:

| | DETECTOR NAME | DETECTOR MODEL | SERIAL NUMBER | DETECTOR TYPE | LAST UPDATE DATE/TIME |
|---|---|---|---|---|---|
| ☐ | 710C-2 | CXDI710C-Wireless | 2800FF09 | 70C | 2016/01/01 12:11:10 |
| ☑ | 50G-3 | CXDI50G | 10000010 | 50G | 2016/02/01 11:50:10 |
| ☐ | 70C-2 | CXDI70C-Wireless | 1800FF04 | 70C | 2016/03/03 18:21:30 |
| | | | | | |
| | | | | | |
| | | | | | |

NEXT>

CANCEL

FIG. 19

INTRODUCED DETECTOR: 50G-3 (MODEL: CXDI50G TYPE: 50G)

REFERENCE DETECTOR:

| | DETECTOR NAME | DETECTOR MODEL | SERIAL NUMBER | DETECTOR TYPE | LAST UPDATE DATE/TIME | SETTING INFORMATION |
|---|---|---|---|---|---|---|
| ☑ | CXDI50G-01 | CXDI50G | 10000000 | 50G | 2015/10/01 12:11:10 | WS-50G, WS-50G-Stand |
| ☐ | CXDI50G-02 | CXDI50G | 10000001 | 50G | 2015/09/01 10:22:10 | WS-50G, WS-50G-Table |
| ☒ | 70C-Wireless | CXDI70C-Wireless | 1800FF01 | 70C | 2014/07/02 19:20:30 | WS-70CGr. |
| ☒ | 710C-Wireless | CXDI710C-Wireless | 2800FF03 | 70C | 2014/03/03 17:25:30 | WS-710C-2, WS-70CGr. |

[ADD] [REPLACE] [< BACK] [CANCEL]

FIG. 20

| | DETECTOR NAME | DETECTOR MODEL | SERIAL NUMBER | DETECTOR TYPE | LAST UPDATE DATE/TIME | SETTING INFORMATION |
|---|---|---|---|---|---|---|
| ☑ | CXDI50G-01 | CXDI50G | 10000000 | 50G | 2015/10/01 12:11:10 | ☐WS-50G ☑WS-50G-Stand |
| ☐ | CXDI50G-02 | CXDI50G | 10000001 | 50G | 2015/09/01 10:22:10 | ☒WS-50G ☒WS-50G-Table |
| ☒ | 70C-Wireless | CXDI70C-Wireless | 1800FF01 | 70C | 2014/07/02 19:20:30 | ☒WS-70CGr. |
| ☒ | 710C-Wireless | CXDI710C-Wireless | 2800FF03 | 70C | 2014/03/03 17:25:30 | ☒WS-710C-2 ☒WS-70CGr. |

INTRODUCED DETECTOR:   50G-3 (MODEL: CXDI50G  TYPE: 50G)

REFERENCE DETECTOR:

[ADD] [REPLACE]
[< BACK] [CANCEL]

FIG. 21

INTRODUCED DETECTOR: 50G-3 (MODEL: CXDI50G  TYPE: 50G)

REFERENCE DETECTOR:

| DETECTOR NAME | DETECTOR MODEL | SERIAL NUMBER | DETECTOR TYPE | LAST UPDATE DATE/TIME | SETTING INFORMATION |
|---|---|---|---|---|---|
| CXDI50G-01 | CXDI50G | 10000000 | 50G | 2015/10/01 12:11:10 | ☐WS-50G<br>☑WS-50G-Stand |
| CXDI50G-02 | CXDI50G | 10000001 | 50G | 2015/09/01 10:22:10 | ☐WS-50G<br>☑WS-50G-Table |
| 70C-Wireless | CXDI70C-Wireless | 1800FF01 | 70C | 2014/07/02 19:20:30 | WS-70CGr. |
| 710C-Wireless | CXDI710C-Wireless | 2800FF03 | 70C | 2014/03/03 17:25:30 | ☒WS-710C-2<br>☒WS-70CGr. |

[ADD]  [REPLACE]

[< BACK]  [CANCEL]

RADIATION IMAGING APPARATUS, RADIATION IMAGING SYSTEM, RADIATION IMAGING METHOD, AND STORAGE MEDIUM

BACKGROUND OF THE INVENTION

Field of the Invention

The present invention relates to a radiation imaging apparatus configured to replace a radiation detector registered in a radiation imaging system, a radiation imaging system, a radiation imaging method, and a storage medium.

Description of the Related Art

Hitherto, in the medical field relating to radiographic imaging, there is known a radiation imaging system configured to irradiate a subject to be examined with radiation and detect intensity of the radiation transmitted through the subject to be examined by a radiation detector, to thereby conduct the radiographic imaging. In the imaging using the radiation imaging system, imaging conditions need to be selected before the imaging is conducted. In general, an optimal image processing parameter differs for each combination of an imaged body part of a subject to be examined who is to be imaged, the posture during the imaging of the subject to be examined, and a type of the radiation detector used for the imaging.

The imaging conditions are selected from among those pieces of information. For example, when the imaging is to be conducted under conditions that a chest is used as the imaged body part, a standing position is used as the posture during the imaging, and a radiation detector A is used as the radiation detector, the imaging conditions including those pieces of information are selected before the imaging. The imaging conditions are formed of two parts of imaged body part information and combined information including setting information. The setting information is associated with mounted position information on the radiation detector corresponding to a posture of a patient to be imaged and device information on the radiation detector to be used.

When a new radiation detector is to be introduced into the radiation imaging system, it may be burdensome for an operator to perform work of creating new setting information and associating the newly created setting information with an enormous amount of imaged body part information. In view of this, in Japanese Patent Application Laid-Open No. 2013-39198, there is proposed an X-ray imaging control apparatus configured to select a divertible imaging condition for an X-ray sensor and set the divertible imaging condition in another X-ray sensor.

However, the technology proposed in Japanese Patent Application Laid-Open No. 2013-39198 assumes a case of newly creating the setting information. Hence, for example, in order to replace a radiation detector by an alternative detector when the radiation detector fails, or to replace an aging radiation detector by a new radiation detector, it is necessary for the operator to manually add and clear the association of the setting information on the radiation detector. Therefore, the work of adding and clearing the association may impose a burden on the operator or lead to such an operational error as to forget updating the association with a specific piece of setting information.

SUMMARY OF THE INVENTION

Therefore, the present invention provides a technology capable of reducing a workload of an operator when a radiation detector is to be introduced.

According to one embodiment of the present invention, there is provided a radiation imaging apparatus, including: a radiation detector configured to detect radiation; a first detector designation unit configured to designate a first radiation detector; a second detector designation unit configured to designate a second radiation detector registered in the radiation imaging apparatus in advance; and an information control unit configured to associate setting information on the second radiation detector with the first radiation detector after the first radiation detector and the second radiation detector are designated.

Further features of the present invention will become apparent from the following description of exemplary embodiments with reference to the attached drawings.

BRIEF DESCRIPTION OF THE DRAWINGS

FIG. 7 is a diagram for illustrating an example of a GUI of a replacement information screen according to the second embodiment of the present invention.

FIG. 18 is a diagram for illustrating an example of a GUI of an introduced detector information screen according to another embodiment of the present invention.

FIG. 19 is a diagram for illustrating an example of a GUI of a reference detector information screen according to another embodiment of the present invention.

FIG. 20 is a diagram for illustrating an example of a GUI of a setting information selection screen according to another embodiment of the present invention.

FIG. 21 is a diagram for illustrating an example of a GUI of a setting information selection screen according to another embodiment of the present invention.

DESCRIPTION OF THE EMBODIMENTS

Preferred embodiments of the present invention will now be described in detail in accordance with the accompanying drawings.

The following embodiments are not intended to limit the present invention defined in the appended claims, and not all combinations of features described in the embodiments are essential to solutions of the present invention.

First Embodiment

<Outline of Configuration of Radiation Imaging System>

Figure 1:
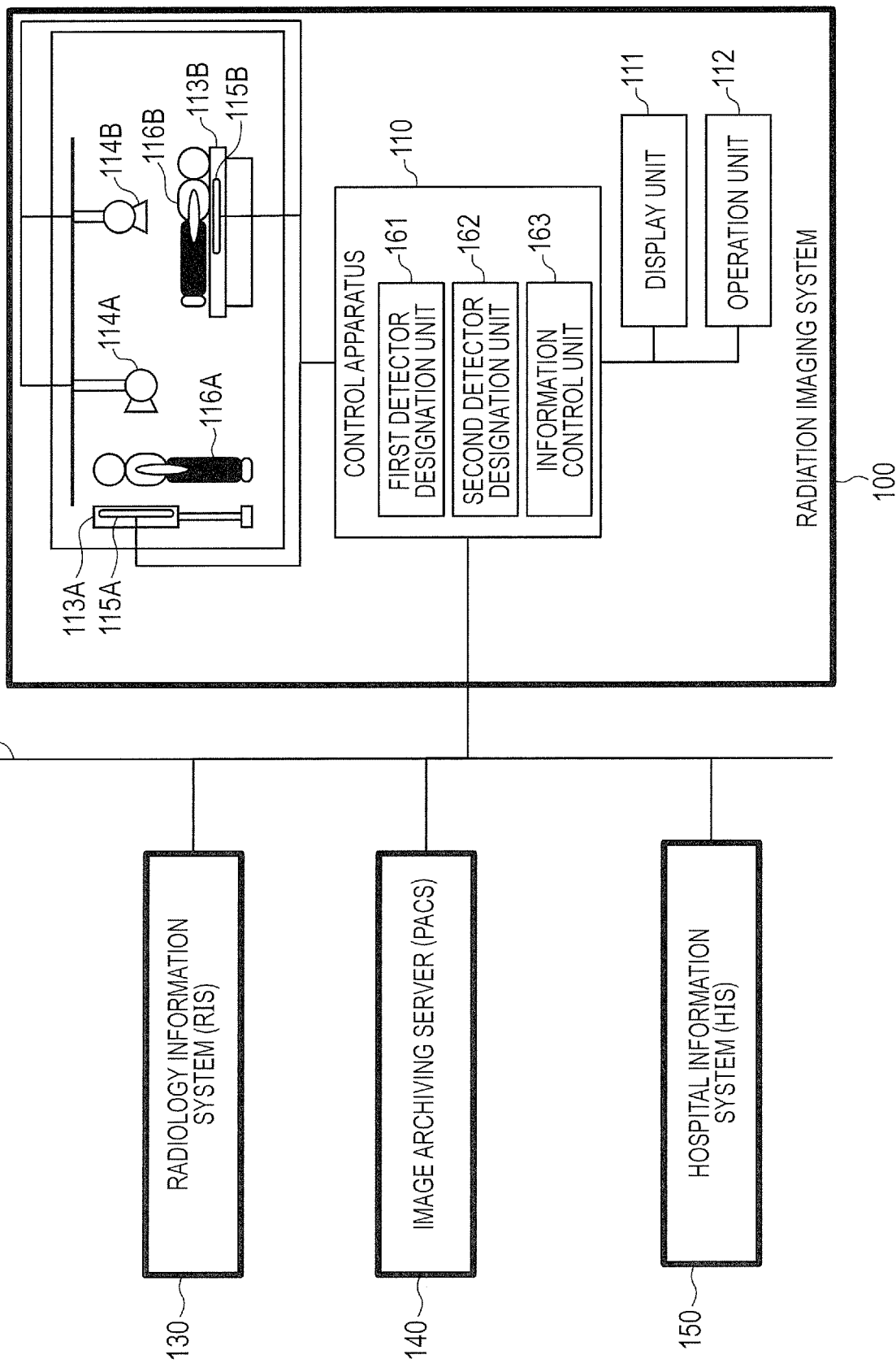
FIG. 1 is a configuration diagram for illustrating an example of a radiation imaging system according to one embodiment of the present invention.

FIG. 1 is a diagram for illustrating an example of a system configuration of a radiation imaging system 100 according to a first embodiment of the present invention. The radiation imaging system 100 includes a control apparatus 110, a display unit 111, an operation unit 112, an imaging stand 113A, an imaging table 113B, radiation generation units 114A and 114B, and radiation detectors 115A and 115B. In the following description, for the sake of convenience, the radiation generation units 114A and 114B are sometimes referred to simply as "radiation generation unit 114", and the radiation detectors 115A and 115B are sometimes referred to simply as "radiation detector 115".

The control apparatus 110 is electrically connected to the display unit 111, the operation unit 112, the radiation generation units 114A and 114B, and the radiation detectors 115A and 115B in a wired or wireless manner, and is configured to control an operation of each device. The control apparatus 110 is further connected to a radiology information system (RIS) 130, an image archiving server (PACS) 140, and a hospital information system (HIS) 150 through a network 120, and is capable of exchanging a radiographic image, patient information, and the like.

The control apparatus 110 includes a first detector designation unit 161, a second detector designation unit 162, and an information control unit 163. The first detector designation unit 161 is configured to designate a first radiation detector to be introduced into the radiation imaging system 100. The second detector designation unit 162 is configured to designate a second radiation detector registered in the radiation imaging system 100 in advance and associated with setting information in the radiation imaging system 100.

The control apparatus 110 is included in a radiation imaging apparatus including a radiation detector configured to detect radiation. The radiation detector may be registered in the radiation imaging apparatus instead of the radiation imaging system 100. The first detector designation unit 161 is configured to designate the first radiation detector. The second detector designation unit 162 is configured to designate the second radiation detector registered in the radiation imaging apparatus in advance.

The information control unit 163 is configured to execute a replacement instruction to replace the second radiation detector by the first radiation detector after the first radiation detector and the second radiation detector are designated, and to associate a part or all of setting information on the second radiation detector with the first radiation detector.

The display unit 111 is configured to display various kinds of information, for example, imaging examination information and a radiographic image acquired through the imaging. The operation unit 112 is configured to receive input information from an operator. In the first embodiment, the display unit 111 is, for example, a monitor, and the operation unit 112 is, for example, a keyboard, a mouse, or a touch panel.

The radiation generation units 114A and 114B each include a radiation tube configured to generate radiation, and are configured to irradiate patients 116A and 116B, respectively, being subjects to be examined with radiation. The patient 116A assumes a standing position, and the patient 116B assumes a supine position. The radiation generation units 114A and 114B and the radiation detectors 115A and 115B mounted in the imaging stand 113A and the imaging table 113B, respectively, are arranged in positions suitable for the imaging.

The radiation detectors 115A and 115B are configured to detect radiation emitted from the radiation generation units 114A and 114B, respectively. The control apparatus 110 is configured to conduct image processing on radiographic image data detected and acquired by the radiation detectors 115A and 115B, and to display the radiographic image data on the display unit 111 as radiographic images.

The radiation imaging system 100 according to the first embodiment is described as being configured to communicate to/from the radiology information system (RIS) 130, the image archiving server (PACS) 140, and the hospital information system (HIS) 150, but may exclude a part of those components. Further, the imaging stand 113A and the imaging table 113B, the radiation generation units 114A and 114B, and the radiation detectors 115A and 115B are described in the example of FIG. 1, but the radiation imaging system 100 may include another combination of an imaging table/stand, a radiation generation unit, and a radiation detector. Further, the above-mentioned functions of the radiation imaging system 100 may be implemented by one apparatus.

<Example of Setting Information Screen>

Figure 2:
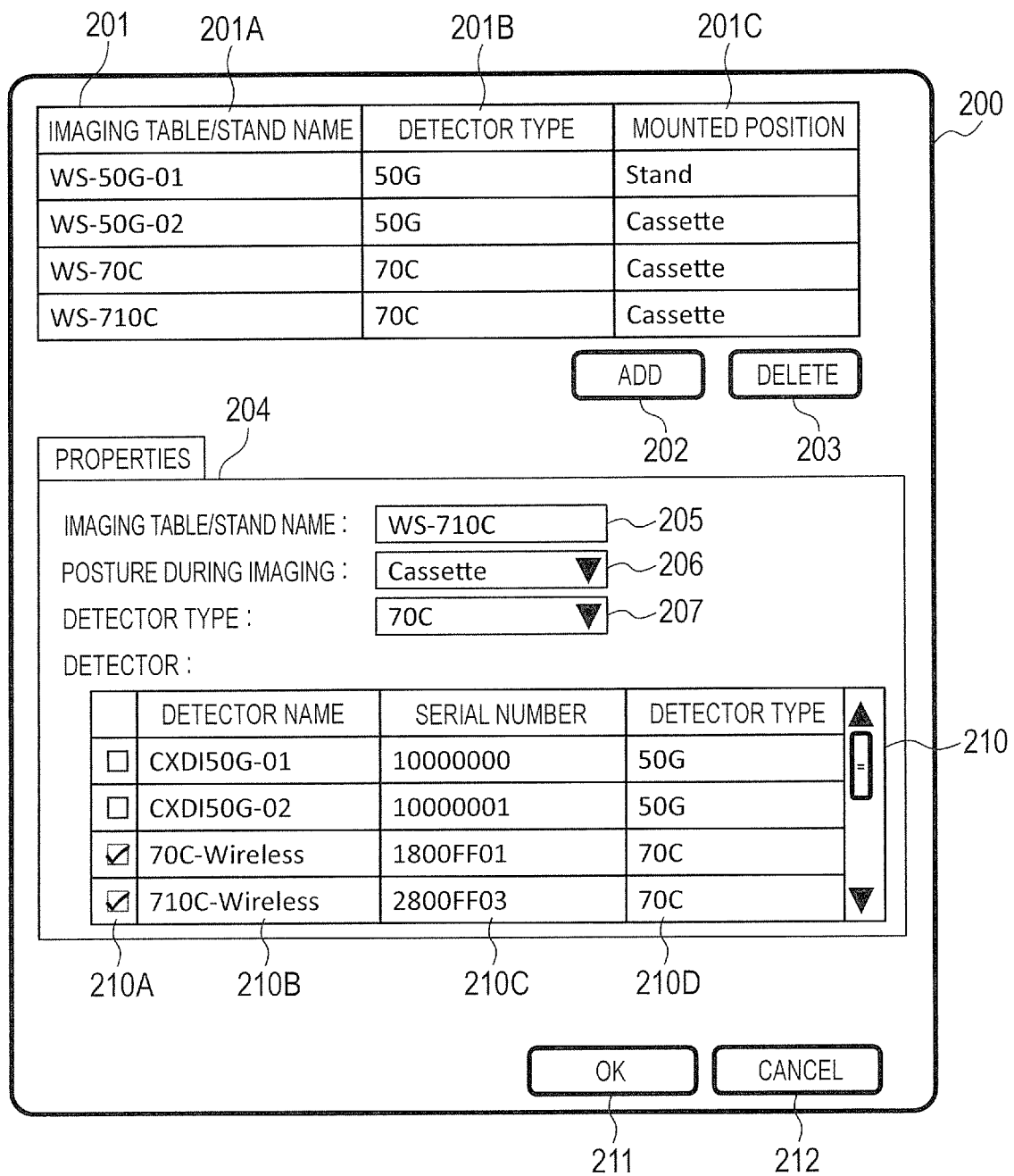
FIG. 2 is a diagram for illustrating an example of a GUI of a setting information screen according to the one embodiment of the present invention.

FIG. 2 is a diagram for illustrating an example of a setting information screen 200 displayed on the display unit 111 of the first embodiment. The setting information is information relating to the mounting of the radiation detector 115 in the radiation imaging system 100. In the first embodiment, the setting information includes information relating to an imaging table/stand mounted with the radiation detector 115 (imaging table/stand information), information relating to a type of the radiation detector 115 (type information), and information relating to a mounted position of the radiation detector 115 corresponding to a posture of a subject to be examined (mounted position information).

The setting information screen 200 includes a setting information list 201, an addition instruction part 202, a deletion instruction part 203, set device information 204, mounted imaging table/stand information 205, a mounted position selection part 206, and a type selection part 207. The setting information screen 200 further includes a set device list 210, a mounting completion instruction part 211, and a mounting cancellation instruction part 212.

In the setting information list 201, a list of setting information set in the radiation imaging system 100 is displayed.

In the setting information list 201, imaging table/stand information 201A, type information 201B, and mounted position information 201C are displayed. The addition instruction part 202 is a button for newly creating the setting information. The deletion instruction part 203 is a button for deleting the setting information selected in the setting information list 201. When no item is selected in the setting information list 201, the deletion instruction part 203 is disabled.

In the set device information 204, details of the setting information selected in the setting information list 201 are displayed. The mounted imaging table/stand information 205 includes a name of the imaging table/stand mounted with the radiation detector 115, and can be changed by being input to a text box or the like through the operation unit 112, for example, a keyboard. The mounted position selection part 206 is an area that allows the mounted position information within the setting information to be displayed and changed, and allows selection to be made from a combo box or other such list of the mounted position information.

The type selection part 207 is an area that allows the type of the radiation detector 115 associated in the setting information to be displayed and changed, and allows selection to be made from a combo box or other such list of the type information. In the set device list 210, a list of the radiation detectors 115 registered in the radiation imaging system 100 is displayed. In the list of the radiation detectors 115, a checkbox 210A indicating whether or not the radiation detector 115 is associated with the setting information, a name (model) 210B of each radiation detector 115, a serial number 210C of each radiation detector 115, and type information 210D of each radiation detector 115 are displayed.

When the checkbox 210A is checked, the radiation detector 115 and the setting information displayed in the set device information 204 are associated with each other. At this time, when the type information 210D on the radiation detector 115 to be associated and the type information displayed in the type selection part 207 do not match each other, the checkbox 210A cannot be checked. The mounting completion instruction part 211 is a button for instructing to determine details to be set for the setting information. The mounting cancellation instruction part 212 is a button for instructing to cancel details of a setting change to be made to the setting information.

<Example of Setting Information Addition Screen>

Figure 3:
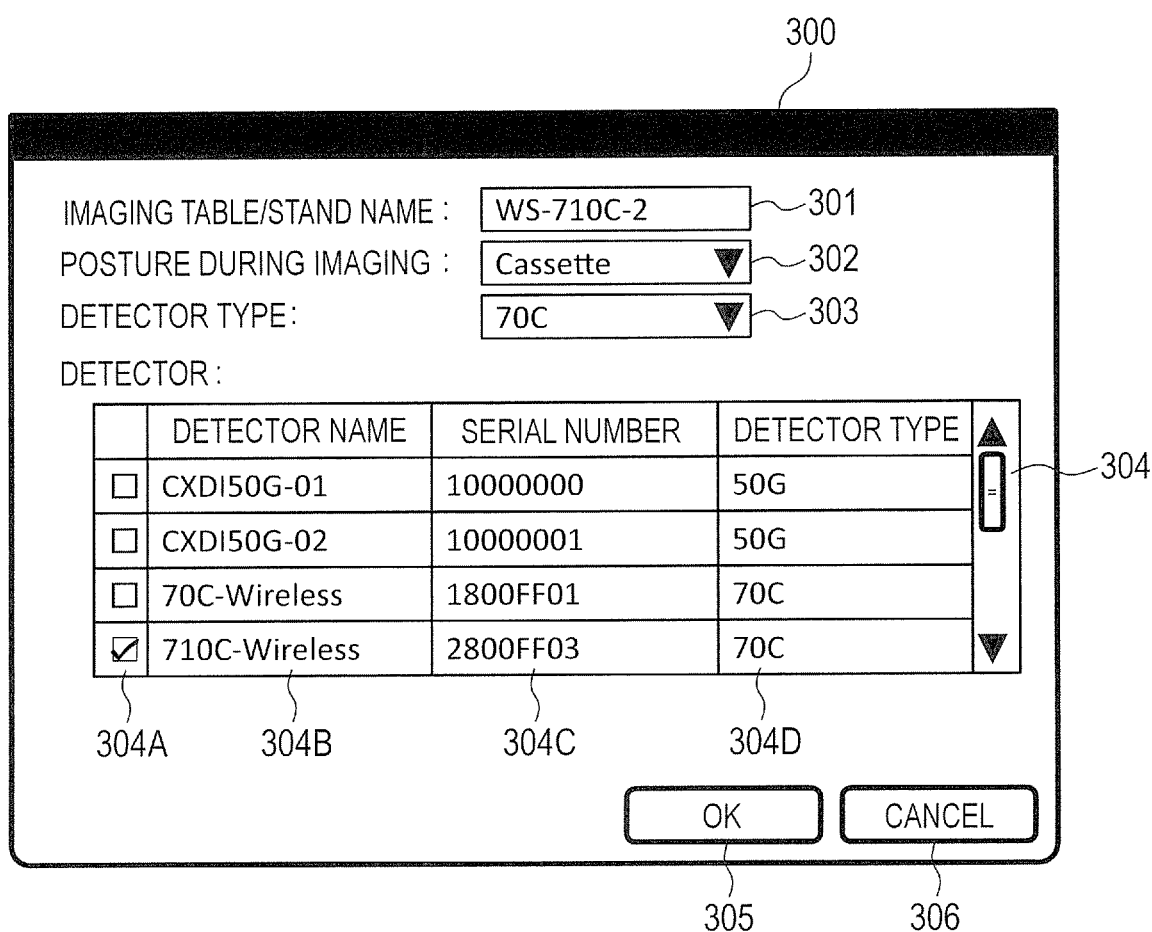
FIG. 3 is a diagram for illustrating an example of a GUI of a setting information addition screen according to the one embodiment of the present invention.

FIG. 3 is a diagram for illustrating an example of a setting information addition screen 300 displayed on the display unit 111 when the button of the addition instruction part 202 displayed on the setting information screen 200 is pressed. The setting information addition screen 300 includes mounted imaging table/stand information 301, a mounted position selection part 302, a type selection part 303, an added device list 304, an addition completion instruction part 305, and an addition cancellation instruction part 306.

The mounted imaging table/stand information 301 includes the name of the imaging table/stand mounted with the radiation detector 115, and can be set by being input to a text box or the like through the operation unit 112, for example, a keyboard. The mounted position selection part 302 is an area that allows the mounted position information within the setting information to be set, and allows selection to be made from a combo box or other such list of the mounted position information. The type selection part 303 is an area that allows the type information on the radiation detector within the imaging table/stand information to be set, and allows selection to be made from a combo box or other such list of the type information.

In the added device list 304, the list of the radiation detectors 115 registered in the radiation imaging system 100 is displayed. In the added device list 304, a checkbox 304A for associating each radiation detector 115 with the setting information, a name (model) 304B of each radiation detector 115, a serial number 304C of each radiation detector 115, and type information 304D on each radiation detector 115 are displayed.

When the checkbox 304A is checked, the radiation detector 115 is associated with the setting information being created in the mounted imaging table/stand information 301, the mounted position selection part 302, and the type selection part 303. At this time, when the type information 304D on the radiation detector 115 to be associated and the type information displayed in the type selection part 303 do not match each other, the checkbox 304A cannot be checked.

The addition completion instruction part 305 is a button for instructing to determine created details of the setting information. When no item is checked in the checkbox 304A within the added device list 304, the addition completion instruction part 305 is disabled. When an addition completion instruction is executed through the addition completion instruction part 305 to complete addition setting, the setting information added to the setting information list 201 on the setting information screen 200 is displayed.

The addition cancellation instruction part 306 is a button for instructing to cancel the creation of the setting information. When a creation cancellation instruction is executed through the addition cancellation instruction part 306, instructions on the setting information addition screen 300 are discarded, the setting information addition screen 300 finishes being displayed, and the setting information screen 200 is displayed.

The operator can selectively specify each button or the like through the operation unit 112. When the display unit 111 is a touch panel, the operator may selectively specify each button or the like by directly touching and operating the setting information screen 200 or the setting information addition screen 300.

<Example of Replacement Processing>

Figure 4:
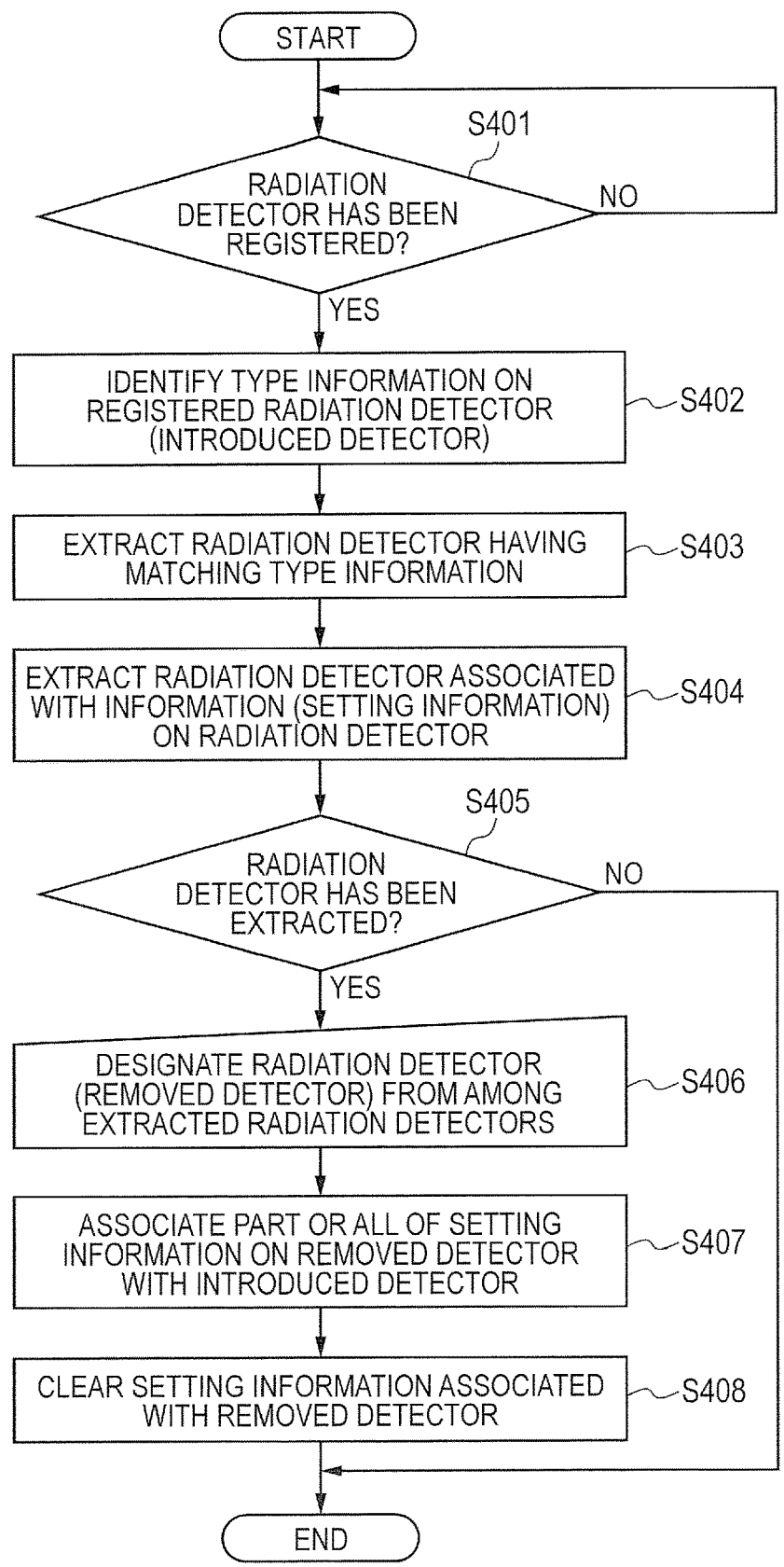
FIG. 4 is a flowchart for illustrating processing according to a first embodiment of the present invention.

Next, a description is made of processing for replacing the radiation detector (removed detector) registered in the radiation imaging system 100 and associated with the setting information in the radiation imaging system 100 (or radiation imaging apparatus) by the first radiation detector (introduced detector) to be introduced into the radiation imaging system 100. FIG. 4 is a flowchart for illustrating an example of the processing for replacing, by the control apparatus 110, the removed detector (second radiation detector) by the introduced detector (first radiation detector) when the introduced detector (first radiation detector) is to be registered in the radiation imaging system 100.

The removed detector (second radiation detector) is replaced by the introduced detector (first radiation detector), and has the association with the setting information cleared.

In Step S401, the information control unit 163 determines whether or not the first radiation detector (introduced detector) unregistered in the radiation imaging system 100 has been registered. When it is determined that the first radiation detector has been registered, the processing advances to Step S402. When it is determined that the first radiation detector has not been registered, the information control unit 163 stands by until the first radiation detector is registered.

In Step S402, the information control unit 163 identifies the type information on the first radiation detector. In Step S403, the information control unit 163 detects all the radiation detectors 115 having the type information that matches the type information on the first radiation detector identified in Step S402 from the radiation imaging system 100. In Step S404, the second detector designation unit 162 extracts the radiation detector 115 associated with the setting information from among the radiation detectors 115 detected in Step S403.

In this manner, the second detector designation unit 162 extracts the radiation detector having the information relating to the type which matches the information relating to the type of the first radiation detector from among the radiation detectors registered in the radiation imaging system 100 in advance and associated with the setting information in the radiation imaging system 100.

In Step S405, when the information control unit 163 determines that there exists at least one radiation detector 115 extracted in Step S404, the processing advances to Step S406. When the information control unit 163 determines that there exists no radiation detector 115 extracted in Step S404, the processing is brought to an end. In Step S406, the second detector designation unit 162 designates the second radiation detector to be replaced by the first radiation detector from among the radiation detectors 115 extracted in Step S404 based on input conducted through the operation unit 112. In this manner, the second detector designation unit 162 designates the second radiation detector registered in the radiation imaging system 100 and associated with the setting information in the radiation imaging system 100.

In Step S407, the information control unit 163 associates the setting information associated with the second radiation detector designated in Step S406 with the first radiation detector registered in Step S401. The first detector designation unit 161 designates the first radiation detector registered in Step S401. The information control unit 163 executes the replacement instruction to replace the second radiation detector by the first radiation detector after the first radiation detector and the second radiation detector are designated, and associates a part or all of the setting information on the second radiation detector with the first radiation detector.

When the control apparatus 110 is included in the radiation imaging apparatus including the radiation detector configured to detect radiation, the control apparatus 110 may include an extraction unit configured to extract the second radiation detector having the same type as that of the first radiation detector. In this case, the first detector designation unit 161 designates the first radiation detector, and the information control unit 163 associates a part or all of the setting information on the second radiation detector extracted by the extraction unit with the first radiation detector. In relation thereto, for example, the second detector designation unit 162 may function as the extraction unit, or the extraction unit may be provided in place of the second detector designation unit 162.

In Step S408, the information control unit 163 clears the association between the second radiation detector designated in Step S406 and the setting information. At this time, the information control unit 163 clears the setting information associated with the second radiation detector. In this case, the registration of the removed detector (second radiation detector) may be removed from the radiation imaging system 100.

<Example of Replacement Information Screen>

Figure 5:
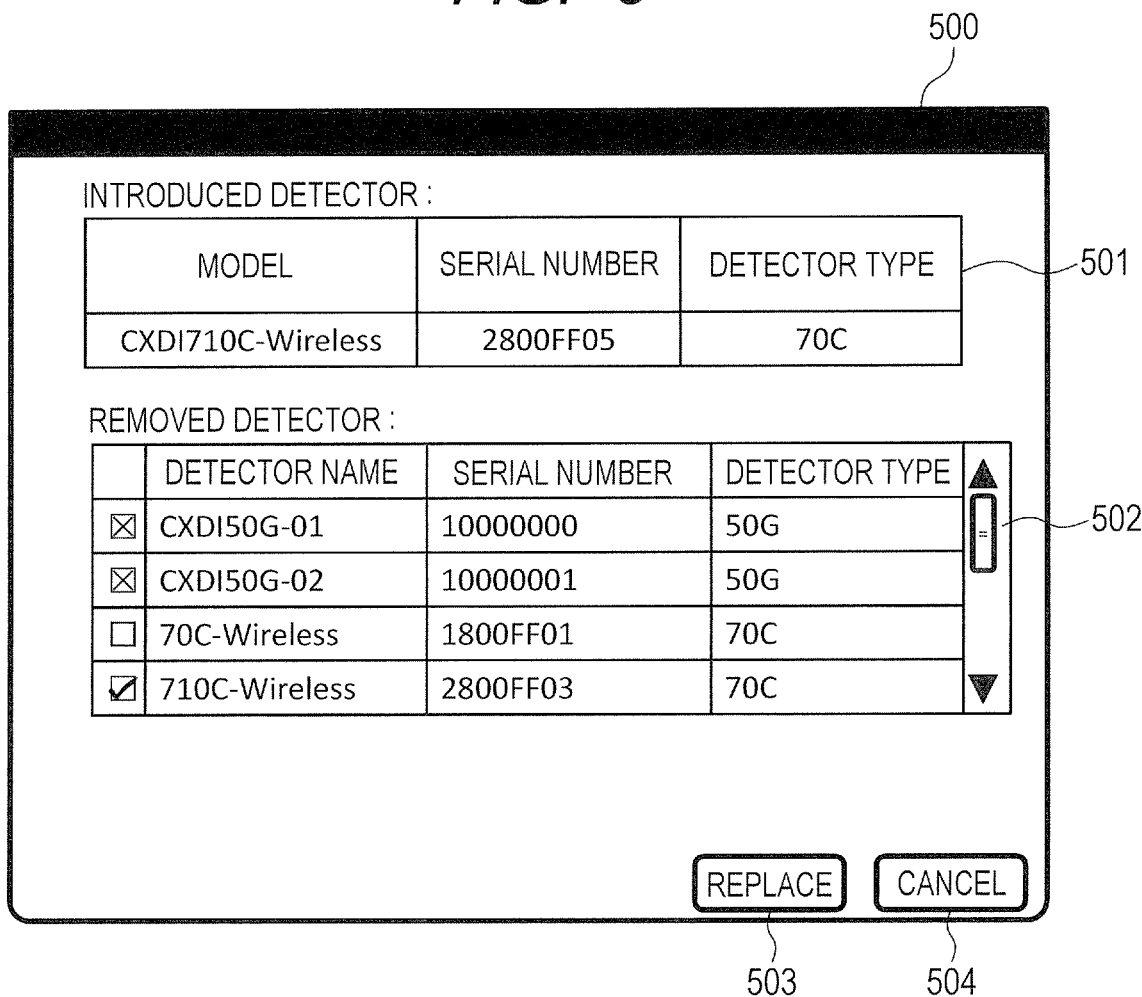
FIG. 5 is a diagram for illustrating an example of a GUI of a replacement information screen according to the first embodiment of the present invention.

FIG. 5 is a diagram for illustrating an example of a replacement information screen 500 displayed on the display unit 111 in order to achieve the flowchart illustrated in FIG. 4 in the first embodiment.

The replacement information screen 500 includes introduced detector information 501, removed detector information 502, a replacement instruction part 503, and a replacement cancellation instruction part 504.

The introduced detector information 501 is an area for displaying information on the first radiation detector (introduced detector) registered in Step S401. In the introduced detector information 501, a name (model) of the first radiation detector, a serial number of the first radiation detector, and type information on the first radiation detector are displayed. The removed detector information 502 is an area that allows the second radiation detector (removed detector) to be designated from among the radiation detectors registered in the radiation imaging system 100 and associated with the setting information in the radiation imaging system 100.

Processing for designating the second radiation detector in the removed detector information 502 corresponds to Step S406, and when a checkbox within the removed detector information 502 is checked, the second detector designation unit 162 designates the second radiation detector (removed detector).

In the removed detector information 502, it is possible to designate the second radiation detector by designating the radiation detector having the type information that matches the type information on the first radiation detector within the introduced detector information 501 from among the radiation detectors 115 registered in the radiation imaging system 100. The second radiation detector that can be designated is the radiation detector 115 extracted in Step S404, that is, the radiation detector 115 associated with the setting information.

The replacement instruction part 503 is a button for executing the replacement instruction to replace the second radiation detector by the first radiation detector and to associate the setting information on the second radiation detector with the first radiation detector. When no item is checked in the checkbox within the removed detector information 502, the replacement instruction part 503 is disabled. When a replacement processing instruction is input through the replacement instruction part 503, Step S407 and Step S408 are executed.

When the replacement is completed, in the set device list 210 on the setting information screen 200, the first radiation detector is displayed in association with the setting information on the second radiation detector (with the checkbox 210A within the first radiation detector being checked). In the set device list 210 on the setting information screen 200, the second radiation detector is also displayed with the association with the setting information being cleared (with the check in the checkbox 210A for the second radiation detector being cleared).

The replacement cancellation instruction part 504 is a button for instructing cancelation of the creation of the setting information. When a setting cancellation instruction is input through the replacement cancellation instruction part 504, instructions on the replacement information screen 500 are discarded, and the replacement information screen 500 finishes being displayed.

The operator can selectively specify each button or the like through the operation unit 112. When the display unit 111 is a touch panel, the operator may selectively specify each button or the like by directly touching and operating the setting information screen 200, the setting information addition screen 300 or the replacement information screen 500.

According to the first embodiment, it is possible to reduce a workload and an operational error of the operator who associates the setting information with the radiation detector when the radiation detector is to be introduced.

Second Embodiment

The first embodiment is described by taking an example of associating the setting information with the first radiation detector when the first radiation detector is to be registered. A second embodiment of the present invention is described by taking an example of replacing the second radiation detector already registered in the radiation imaging system 100 and associated with the setting information by the first radiation detector that is already registered in the radiation imaging system 100 but is not associated with the setting information.

Descriptions of the same components, functions, and operations as those of the above-mentioned embodiment are omitted, and differences between the above-mentioned embodiment and the second embodiment are mainly described.

<Example of Replacement Processing>

Figure 6:
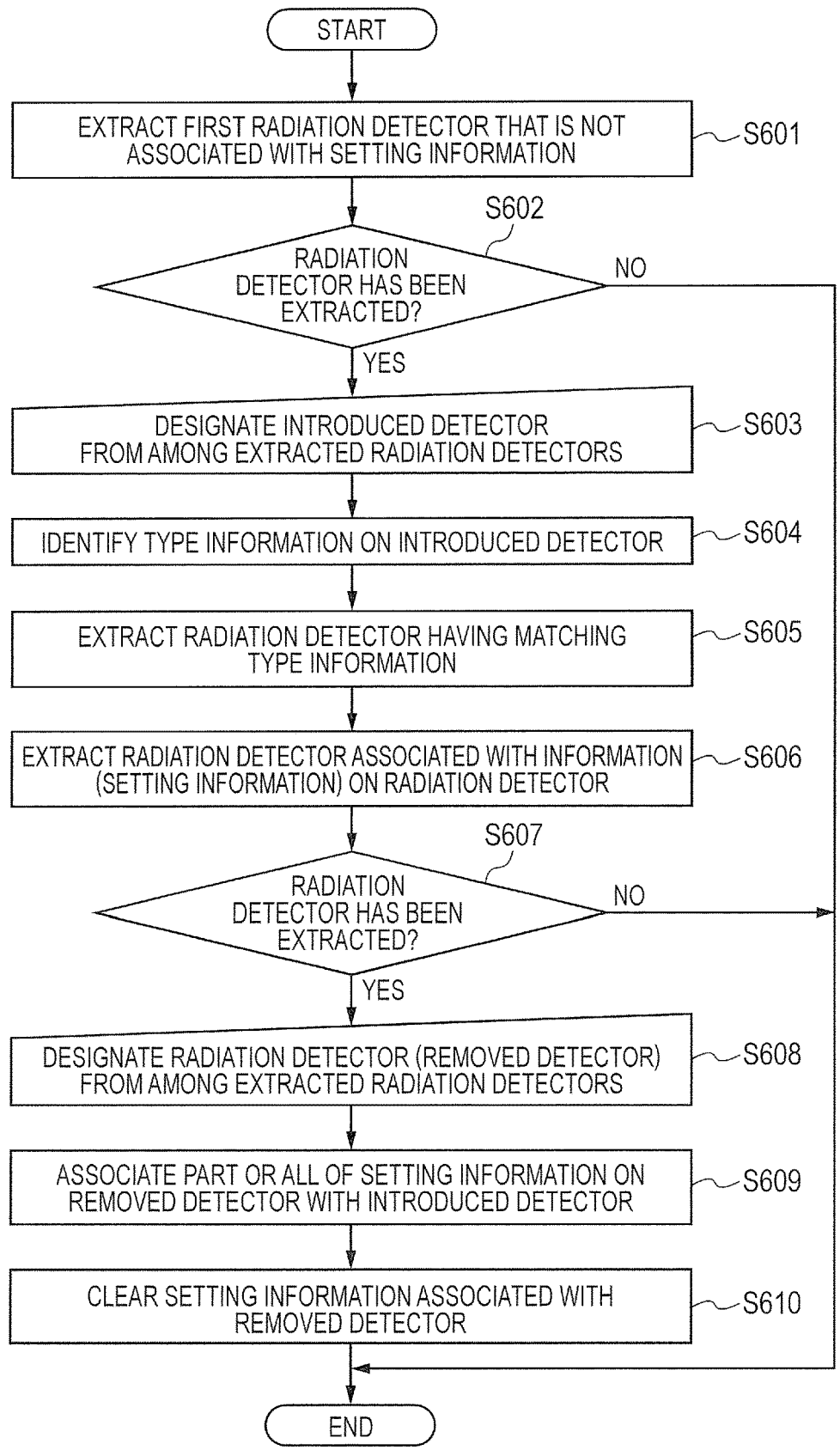
FIG. 6 is a flowchart for illustrating processing according to a second embodiment of the present invention.

FIG. 6 is a flowchart for illustrating an example of processing for replacing the second radiation detector already set in the setting information by the first radiation detector that has not been set in the setting information among the radiation detectors already registered in the radiation imaging system 100 according to the second embodiment.

In Step S601, the information control unit 163 extracts the radiation detector that is not associated with the setting information from among the radiation detectors registered in the radiation imaging system 100. In Step S602, the information control unit 163 determines whether or not there exists at least one extracted result, and when there exists no extracted result, brings the processing to an end. When there exists at least one extracted result, in Step S603, the first detector designation unit 161 designates the first radiation detector (introduced detector) from among the radiation detectors extracted in Step S601.

In Step S604, the information control unit 163 identifies the type information on the first radiation detector. In Step S605, the information control unit 163 detects all the radiation detectors having the type information that matches the type information on the first radiation detector identified in Step S604 from the radiation imaging system 100. In Step S606, the second detector designation unit 162 extracts the radiation detector associated with the setting information from among the radiation detectors detected in Step S605.

In this manner, the second detector designation unit 162 extracts the radiation detector having the information relating to the type which matches the information relating to the type of the first radiation detector from the radiation detectors registered in the radiation imaging system 100 and associated with the setting information in the radiation imaging system 100.

In Step S607, the information control unit 163 determines whether or not there exists at least one extracted result, and when there exists no extracted result, brings the processing to an end. When there exists at least one extracted result, in Step S608, the operator selects, through the operation unit 112, the second radiation detector (removed detector) to be replaced by the first radiation detector designated in Step S603 from among the radiation detectors extracted in Step S607. The second detector designation unit 162 designates the second radiation detector based on the selection by the operator. That is, the second detector designation unit 162 designates the second radiation detector registered in the radiation imaging system 100 and associated with the setting information in the radiation imaging system 100 from among the radiation detectors extracted in Step S607.

In Step S609, the information control unit 163 associates a part or all of the setting information associated with the second radiation detector designated in Step S608 with the first radiation detector designated in Step S603. In Step S610, the information control unit 163 clears the association between the second radiation detector designated in Step S608 and the setting information. At this time, the information control unit 163 clears the setting information associated with the second radiation detector.

<Example of Replacement Information Screen>

FIG. 7 is a diagram for illustrating an example of a replacement information screen 700 displayed on the display unit 111 in order to achieve the flowchart illustrated in FIG. 6 in the second embodiment.

The replacement information screen 700 includes introduced detector information 701, removed detector information 702, a replacement instruction part 703, and a replacement cancellation instruction part 704.

The introduced detector information 701 is an area for displaying, in a list format, information on the first radiation detector extracted in Step S601. In the introduced detector information 701, a name (model) of the first radiation detector, a serial number of the first radiation detector, and type information on the first radiation detector are displayed.

The removed detector information 702 is an area that allows the second radiation detector (removed detector) to be designated from among the radiation detectors registered in the radiation imaging system 100 and associated with the setting information in the radiation imaging system 100. In the removed detector information 702, a checkbox for designating the second radiation detector, a detector name of the radiation detector, a serial number of the radiation detector, the type information on the radiation detector, and the associated setting information are displayed.

When a radiation detector registered in the radiation imaging system 100, which is to be checked, is associated with the setting information but does not have a type that matches the type of the first radiation detector selected in the introduced detector information 701, the checkbox within the removed detector information 702 cannot be checked. The radiation detector that can be checked is the radiation detector extracted in Step S605 and Step S606 (that is, the radiation detector registered in the radiation imaging system 100 and associated with the setting information in the radiation imaging system 100) and having a type that matches the type of the first radiation detector selected in the introduced detector information 701.

The replacement instruction part 703 is a button for executing the replacement instruction to replace the second radiation detector by the first radiation detector and to associate the setting information on the second radiation detector with the first radiation detector. When no item is checked in the checkbox within the removed detector information 702, the replacement instruction part 703 is disabled. When a replacement processing instruction is input through the replacement instruction part 703, Step S609 and Step S610 are executed.

When the replacement is completed, in the set device list 210 on the setting information screen 200, the first radiation detector is displayed in association with the setting information on the second radiation detector (with the checkbox 210A within the first radiation detector being checked). In the set device list 210 on the setting information screen 200, the second radiation detector is also displayed with the association with the setting information being cleared (with the check in the checkbox 210A for the second radiation detector being cleared).

The replacement cancellation instruction part 704 is a button for instructing cancelation of the creation of the setting information. When a setting cancellation instruction is input through the replacement cancellation instruction part 704, instructions on the replacement information screen 700 are discarded, and the replacement information screen 700 finishes being displayed.

The operator can selectively specify each button or the like through the operation unit 112. When the display unit 111 is a touch panel, the operator may selectively specify each button or the like by directly touching and operating the setting information screen 200, the setting information addition screen 300 or the replacement information screen 700.

According to the second embodiment, it is possible to reduce a workload and an operational error of the operator who associates the setting information with the radiation detector when the radiation detector is to be introduced.

Third Embodiment

The first embodiment and the second embodiment are described by taking an example of selecting the second radiation detector (removed detector) from the list of the second radiation detectors already registered in the radiation imaging system 100 as a method of selecting the second radiation detector (removed detector). A third embodiment of the present invention is described by taking an example of conducting the replacement through use of a unit configured to designate radiation detectors to be uniquely replaced (first radiation detector and second radiation detector).

Descriptions of the same components, functions, and operations as those of the above-mentioned embodiments are omitted, and differences between the above-mentioned embodiments and the third embodiment are mainly described.

<Example of Replacement Processing>

Figure 8:
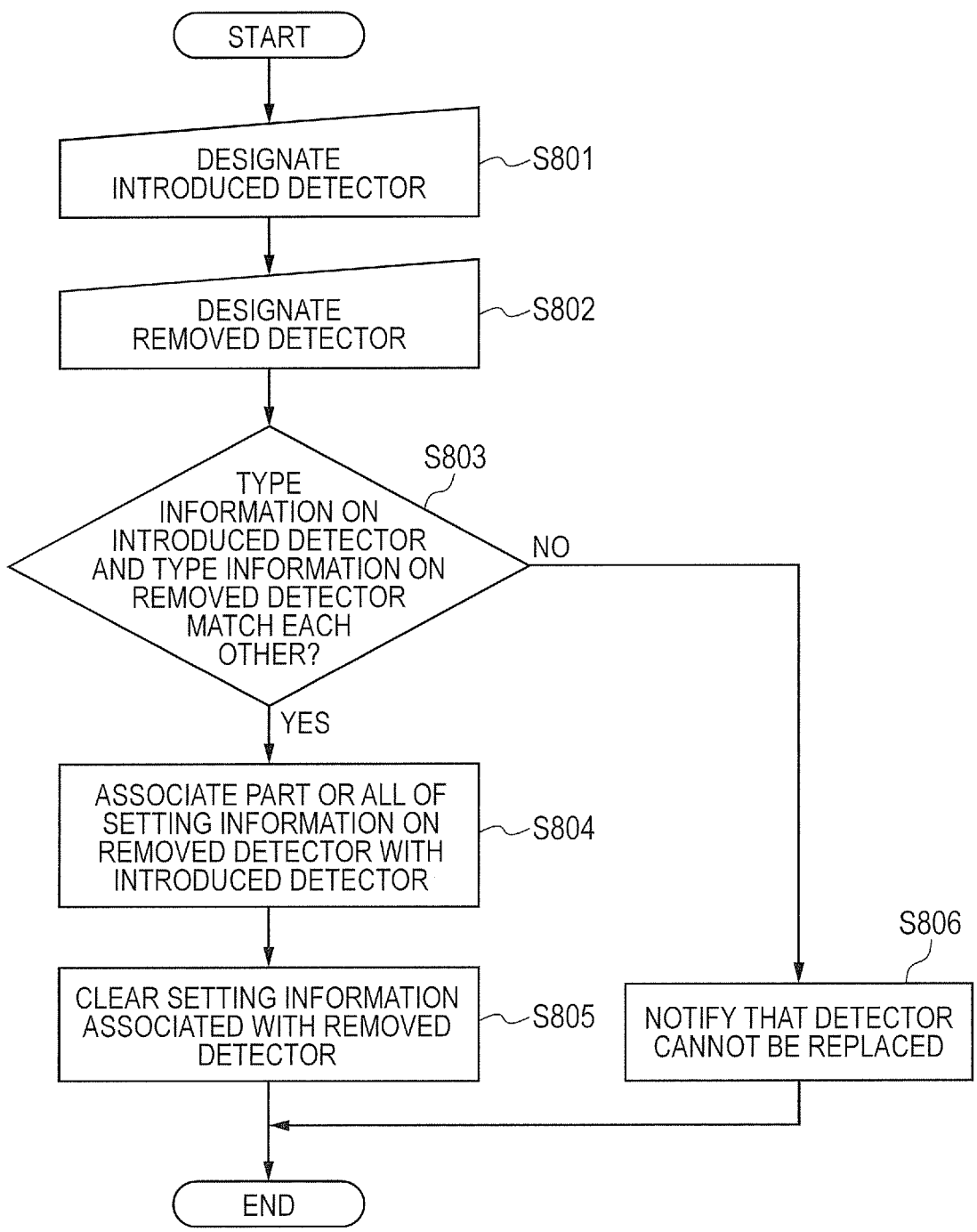
FIG. 8 is a flowchart for illustrating processing according to a third embodiment of the present invention.

FIG. 8 is a flowchart for illustrating an example of processing for uniquely replacing the second radiation detector already registered in the radiation imaging system 100 according to the third embodiment and already set in the setting information by the first radiation detector that has not been set in the setting information.

In Step S801, the first detector designation unit 161 designates the first radiation detector (introduced detector). In this step, in the same manner as in Step S401, the first detector designation unit 161 may designate the first radiation detector when the radiation detector is to be registered in the radiation imaging system 100. The first detector designation unit 161 may also designate the first radiation detector based on a serial number or other such individual information on the radiation detector that is not associated with the setting information within radiation detector information registered in the radiation imaging system 100.

In Step S802, the second detector designation unit 162 designates the radiation detector associated with the setting information as the second radiation detector (removed detector) from among the radiation detectors registered in the radiation imaging system 100. The second detector designation unit 162 may also designate the second radiation detector based on a serial number or other such individual information on the radiation detector associated with the setting information within radiation detector information registered in the radiation imaging system 100.

In Step S803, the information control unit 163 determines whether or not the type information on the first radiation detector (introduced detector) designated in Step S801 and the type information on the second radiation detector (removed detector) designated in Step S802 match each other. When there is a mismatch as a result of the determination, the information control unit 163 notifies the operator that the detector cannot be replaced (or that the setting information cannot be associated), and brings the processing to an end (Step S806). That is, when there is a mismatch in the information relating to the type between the first radiation detector and the second radiation detector, the information control unit 163 gives notification that the setting information cannot be associated.

When there is a match as a result of the determination, the information control unit 163 associates a part or all of the setting information associated with the information on the second radiation detector designated in Step S802 with the first radiation detector designated in Step S801 (Step S804). In Step S805, the information control unit 163 clears the association between the second radiation detector designated in Step S802 and the setting information. At this time, the information control unit 163 clears the setting information associated with the second radiation detector.

<Outline of Configuration of Radiation Imaging System>

Figure 9:
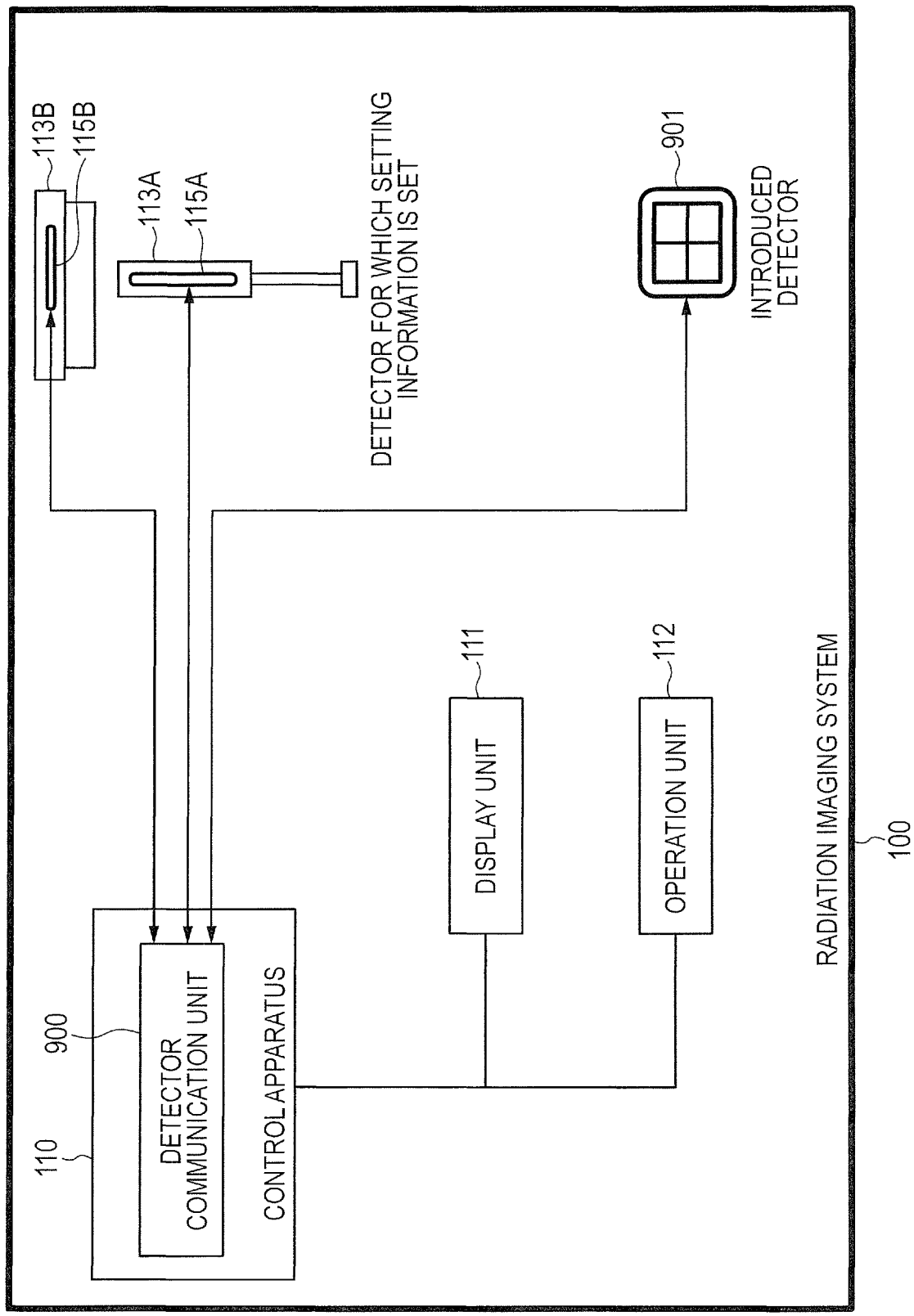
FIG. 9 is a configuration diagram for illustrating an example of a radiation imaging system according to the third embodiment of the present invention.

FIG. 9 is a diagram for illustrating an example of a system configuration of the radiation imaging system 100 for achieving the flowchart illustrated in FIG. 8 in the third embodiment. In FIG. 9, points relating to the third embodiment are mainly described, and duplicates of descriptions made with reference to FIG. 1 are omitted.

The control apparatus 110 further includes a detector communication unit 900 configured to collect the radiographic image data detected and acquired by the radiation detectors 115A and 115B. The detector communication unit 900 may be used for acquiring information on the radiation detector by the control apparatus 110 through communication when the radiation detector is to be registered in the radiation imaging system 100.

The designation of the first radiation detector (introduced detector) conducted in Step S801 is achieved by the detector communication unit 900 communicating to/from a radiation detector 901 for which the setting information has not been set. In the same manner, the designation of the second radiation detector (removed detector) conducted in Step S802 is also achieved by the detector communication unit 900 communicating to/from the radiation detector 115A or the radiation detector 115B for which the setting information has been set.

In Step S801, when the radiation detector 901 is already registered in the radiation imaging system 100, a serial number or other such individual information is input through the operation unit 112 in order to identify the radiation detector 901. With this operation, the first detector designation unit 161 may designate the radiation detector 901 as the first radiation detector. In the same manner, in Step S802, the second radiation detector may be designated by inputting a serial number or other such individual information through the operation unit 112 in order to identify the radiation detector 115A or the radiation detector 115B for which the setting information has been set.

<Example of Replacement Information Screen>

Figure 10:
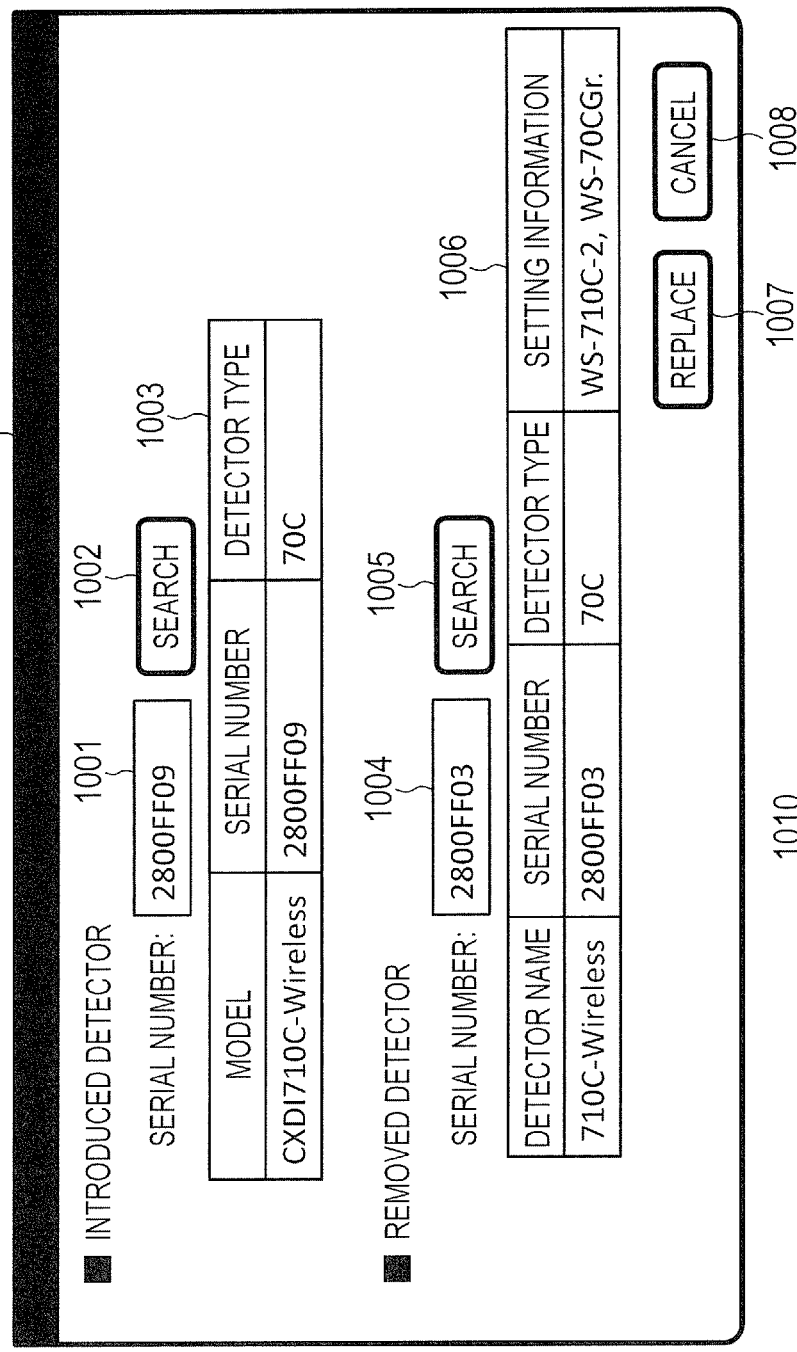
FIG. 10A is a diagram for illustrating an example of a replacement information screen according to the third embodiment of the present invention.
FIG. 10B is a diagram for illustrating an example of a GUI of a notification message according to the third embodiment of the present invention.

FIG. 10A and FIG. 10B are diagrams for illustrating examples of a replacement information screen 1000 and a notification message 1010, respectively, displayed on the display unit 111 in order to achieve the flowchart illustrated in FIG. 8 in the third embodiment.

The replacement information screen 1000 includes a first individual information input part 1001, a first search instruction part 1002, an introduced detector display part 1003, a second individual information input part 1004, a second search instruction part 1005, a removed detector display part 1006, a replacement instruction part 1007, and a replacement cancellation instruction part 1008.

The first individual information input part 1001 is an area for inputting individual information for identifying the radiation detector that is not associated with the setting information, and a serial number or other such individual information on the radiation detector is input to the first individual information input part 1001. The first search instruction part 1002 is used to identify the first radiation detector (introduced detector) from among the radiation detectors registered in the radiation imaging system 100 based on the individual information input to the first individual information input part 1001. That is, the first detector designation unit 161 designates the first radiation detector based on the individual information on the radiation detector.

Those pieces of identification processing may be conducted via the detector communication unit 900 illustrated in FIG. 9. The identification processing corresponds to Step S801. The information on the identified radiation detector is displayed in the introduced detector display part 1003.

The second individual information input part 1004 is an area for inputting individual information for identifying the radiation detector that is associated with the setting information, and a serial number or other such individual information on the radiation detector is input to the second individual information input part 1004. The second search instruction part 1005 is used to identify the second radiation detector (removed detector) from among the radiation detectors registered in the radiation imaging system 100 based on the individual information input to the second individual information input part 1004. That is, the second detector designation unit 162 designates the second radiation detector based on the individual information on the radiation detector.

Those pieces of identification processing may be conducted via the detector communication unit 900 illustrated in FIG. 9. The identification processing corresponds to Step S802. The information on the identified radiation detector is displayed in the removed detector display part 1006.

When the replacement processing instruction is input from the replacement instruction part 1007, determination processing corresponding to Step S803 is executed. When the processing of Step S804 and Step S805 is completed, in the set device list 210 on the setting information screen 200, the first radiation detector is displayed in association with the setting information on the second radiation detector. In this case, the checkbox 210A for the first radiation detector is checked. In the set device list 210 on the setting information screen 200, the second radiation detector is displayed with the association with the setting information being cleared (with the check in the checkbox 210A for the second radiation detector being cleared).

When it is determined that the type information is different between the introduced detector display part 1003 and the removed detector display part 1006 as a result of the determination processing of Step S803, the notification message 1010 for notifying the operator that the processing for replacing the second radiation detector by the first radiation detector cannot be conducted is displayed. The displaying of the notification message 1010 corresponds to Step S806.

The operator can selectively specify each button or the like through the operation unit 112. When the display unit 111 is a touch panel, the operator may selectively specify each button or the like by directly touching and operating the setting information screen 200, the setting information addition screen 300, or the replacement information screen 1000.

According to the third embodiment, it is possible to reduce the workload and the operational error of the operator who associates the setting information with the radiation detector when the radiation detector is to be introduced.

Fourth Embodiment

The first embodiment to the third embodiment are described by taking an example of adding and clearing the association with the setting information through the replacement processing. A fourth embodiment of the present invention is described by taking an example of inheriting imaging setting information relating to the imaging conducted by the second radiation detector (removed detector) to the first radiation detector (introduced detector) in the replacement processing in addition to the above-mentioned processing.

Descriptions of the same components, functions, and operations as those of the above-mentioned embodiments are omitted, and differences between the above-mentioned embodiments and the fourth embodiment are mainly described.

The information control unit 163 executes the replacement instruction to replace the second radiation detector by the first radiation detector after the first radiation detector and the second radiation detector are designated, and associates a part or all of the imaging setting information relating to the imaging conducted by the second radiation detector with the first radiation detector. The imaging setting information includes at least one of calibration information, imaging angle information, or communication setting information on the second radiation detector.

<Example of Outline of Configuration of Radiation Detector Information>

Figure 11:
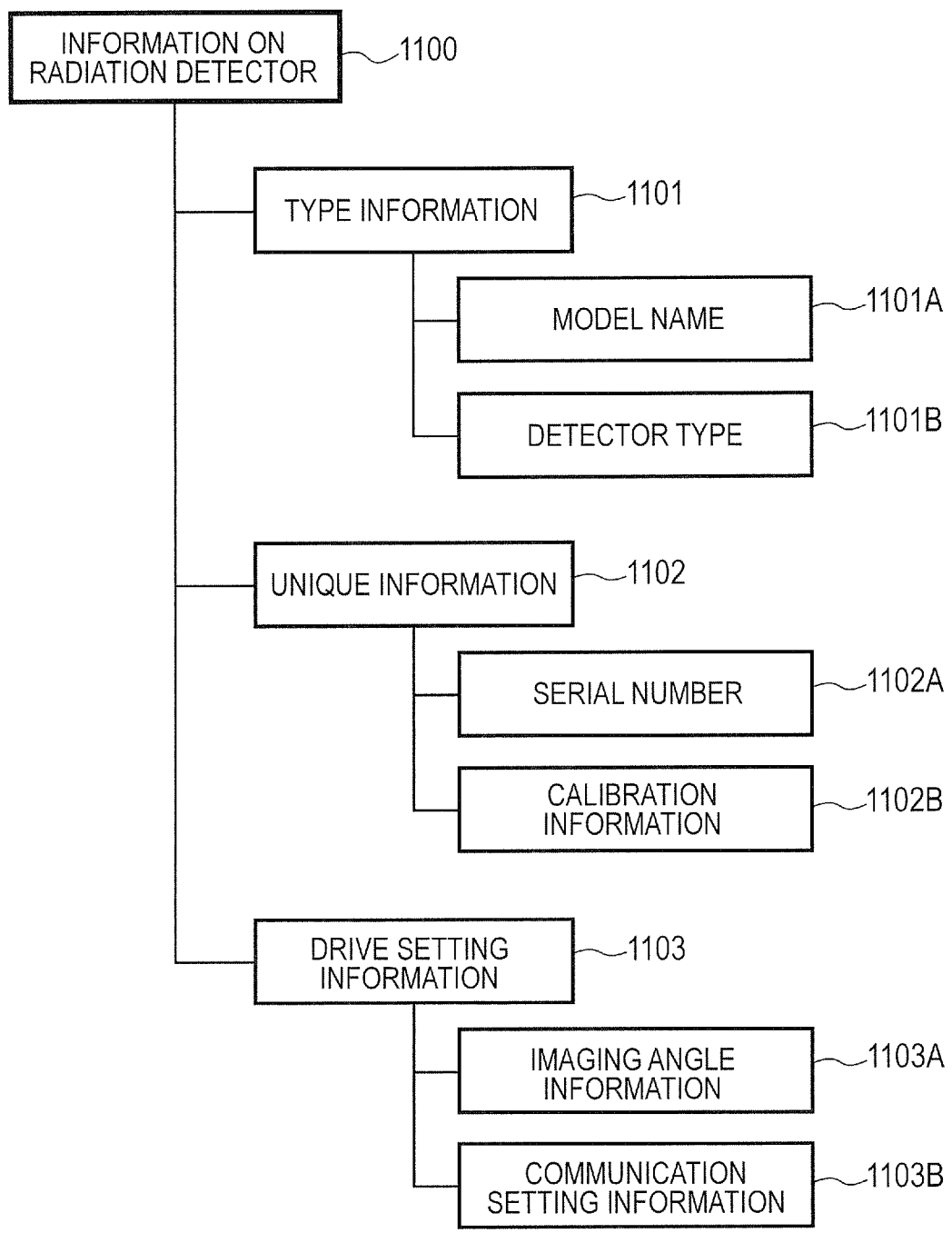
FIG. 11 is a diagram for illustrating an example of detector information according to a fourth embodiment of the present invention.

FIG. 11 is a diagram for illustrating an example of the information (detector information) relating to the radiation detector registered in the radiation imaging system 100 according to the fourth embodiment.

Detector information 1100 registered in the radiation imaging system 100 includes type information 1101, unique information 1102, and drive setting information 1103.

The type information 1101 is information for classifying the radiation detector, and includes a model name 1101A and a detector type 1101B. The unique information 1102 is unique information assigned to each radiation detector, and includes a serial number (individual information) 1102A for uniquely identifying the radiation detector and calibration information 1102B for calibrating an image acquired through the imaging. The drive setting information 1103 is setting information for driving the radiation detector for the imaging, and includes imaging angle information 1103A relating to an angle at which the radiation detector is mounted in the imaging table/stand and communication setting information 1103B relating to the communication to be conducted to/from the control apparatus 110.

When the radiation detector is to be replaced, it may be desired that feeling of use does not change from the radiation detector used before. In view of this, the first radiation detector inherits drive setting information on the second radiation detector in the replacement processing so that there may be no change in the drive setting information 1103 including the imaging angle information 1103A being an angle of a detector set when imaging is conducted and the communication setting information 1103B to be used for communicating to/from the control apparatus 110.

Further, the calibration information 1102B needs to be uniquely set for each radiation detector, but when a radiation detector of the same model is to be replaced, the calibration information 1102B on the second radiation detector can be diverted without the need for resetting for the first radiation detector. In this case, the first radiation detector (introduced detector) inherits the calibration information 1102B on the second radiation detector (removed detector) in the replacement processing.

<Example of Replacement Processing>

Figure 12:
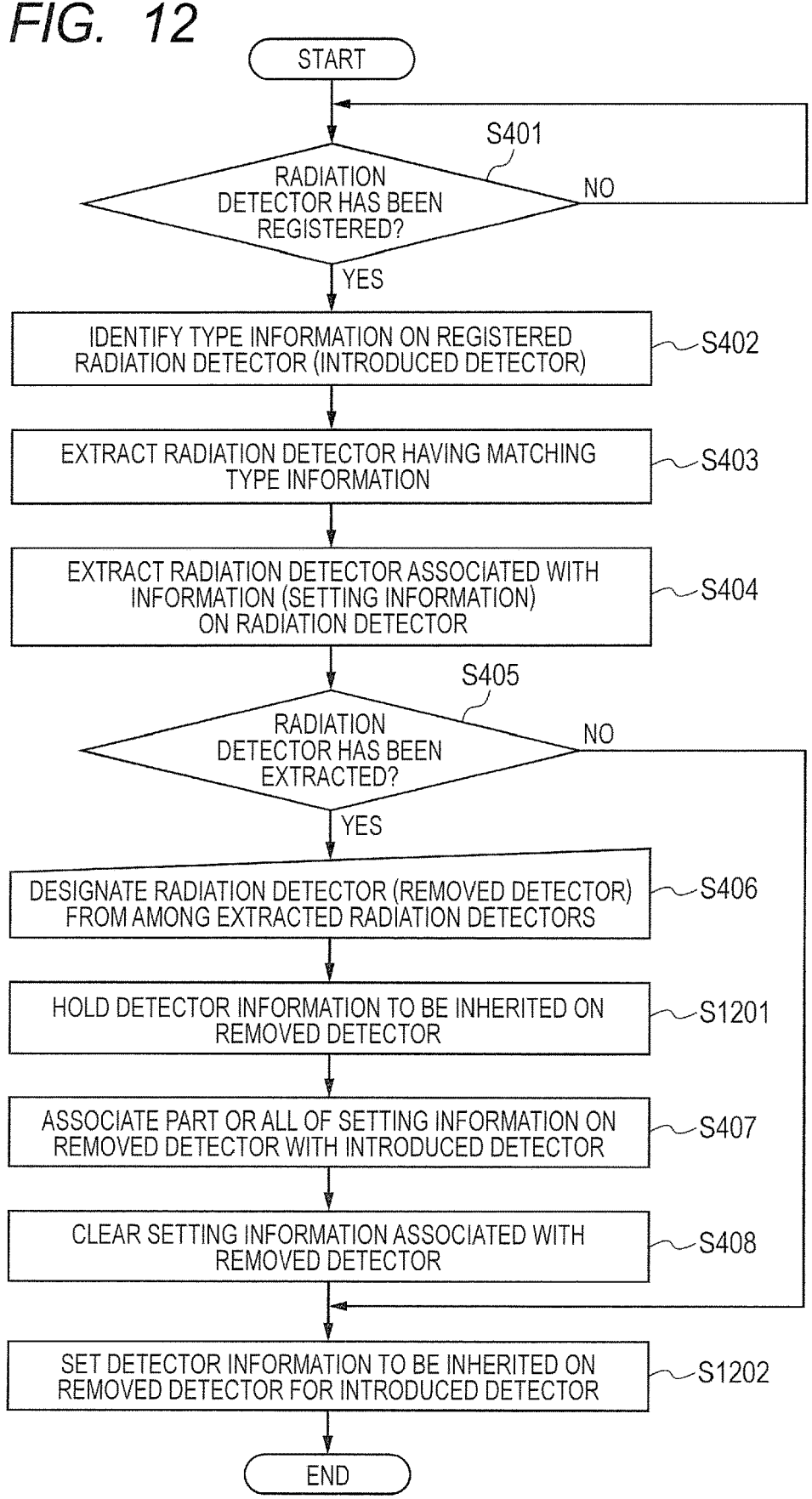
FIG. 12 is a flowchart for illustrating processing according to the fourth embodiment of the present invention.

FIG. 12 is a flowchart for illustrating an example of processing for inheriting the radiation detector information in addition to the replacement processing. The fourth embodiment is described with reference to FIG. 4 of the first embodiment, the descriptions of the same components, functions, and operations as those of the first embodiment are omitted, and differences between the first embodiment and the fourth embodiment are mainly described.

When the second radiation detector is designated in Step S406, the imaging angle information 1103A, the communication setting information 1103B, and other such detector information to be inherited are acquired from the detector information on the second radiation detector and held in a storage device or the like (Step S1201). After that, the information control unit 163 sets the detector information held in Step S1201 for the first radiation detector as the detector information on the first radiation detector (Step S1202). This inhibits the detector information on the radiation detector from being changed before and after the replacement, and hence it is possible to conduct the imaging with an unchanged feeling of use.

According to the fourth embodiment, it is possible to reduce the workload and the operational error of the operator who associates the imaging setting information with the radiation detector when the radiation detector is to be introduced.

Fifth Embodiment

In the fourth embodiment, a description is made of a method of inheriting the imaging setting information on the radiation detector. A fifth embodiment of the present invention is described by taking an example of resetting, when the removed second radiation detector is to be reintroduced, the setting information or imaging setting information before the clearance for the second radiation detector to be reintroduced. As a result, the removed detector can be restored to a status before the clearance.

The fifth embodiment assumes a case where, for example, when a radiation detector registered (or used) in the radiation imaging system 100 fails, this detector is removed, an alternative detector is temporarily introduced, and the removed detector is reintroduced after being repaired.

Descriptions of the same components, functions, and operations as those of the above-mentioned embodiments are omitted, and differences between the above-mentioned embodiments and the fifth embodiment are mainly described.

When the removed detector is reintroduced into the radiation imaging system 100 (or radiation imaging apparatus) after the setting information associated with the second radiation detector is cleared, the information control unit 163 associates a part or all of the setting information (or imaging setting information) on the removed detector before the clearance with the reintroduced removed detector.

<Example of Outline of Configuration of Radiation Detector Information>

Figure 13:
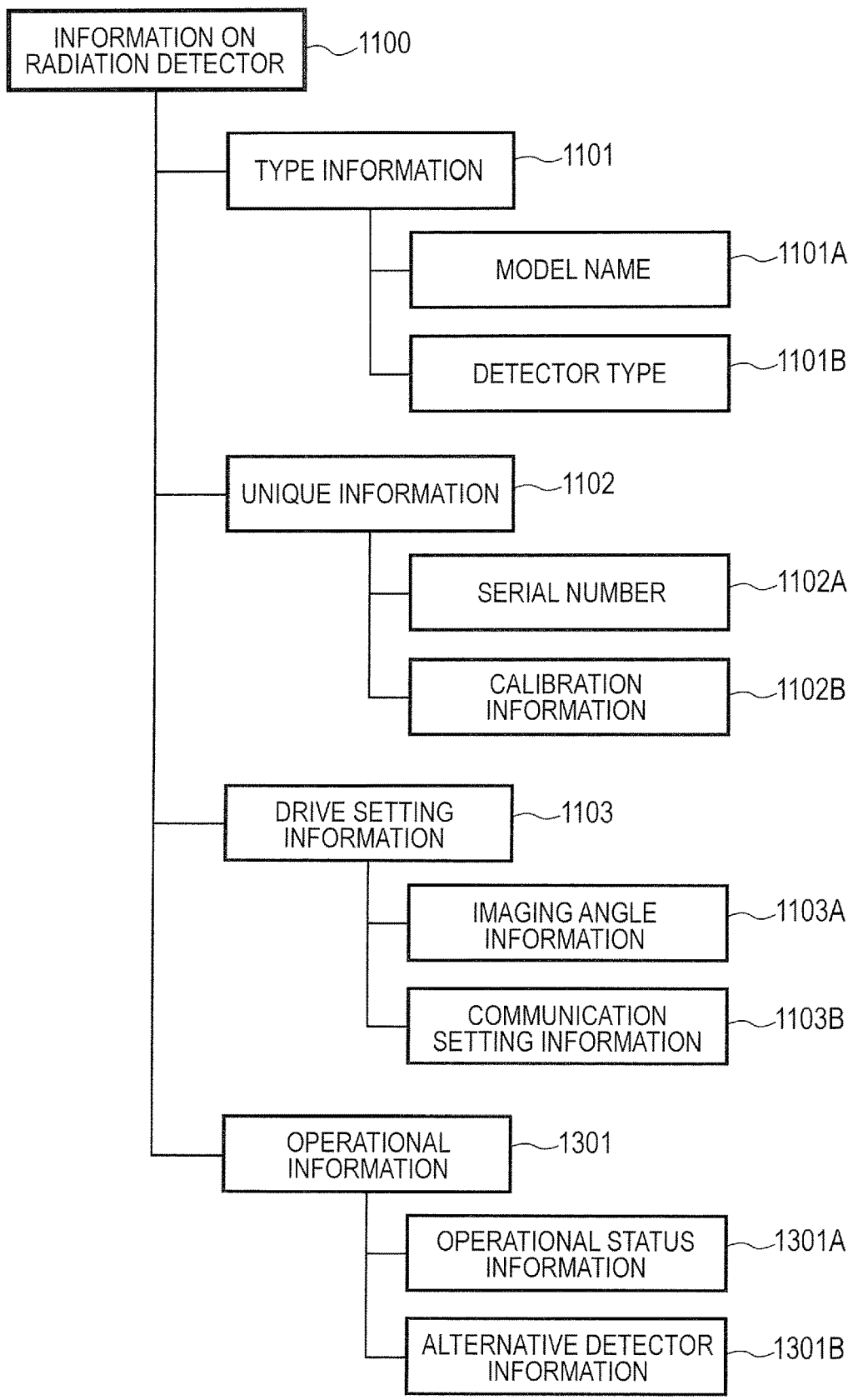
FIG. 13 is a diagram for illustrating an example of detector information according to a fifth embodiment of the present invention.

FIG. 13 is a diagram for illustrating an example of the information (detector information) relating to the radiation detector registered in the radiation imaging system 100 according to the fifth embodiment. In the fifth embodiment, the type information 1101, the drive setting information 1103, and the like have the same structures as those of FIG. 11, and hence descriptions thereof are omitted.

The information on the radiation detector registered in the radiation imaging system 100 includes operational information 1301. The operational information 1301 is information for managing operational status (use status and the like) of the radiation detector. The operational information 1301 includes operational status information 1301A indicating that the radiation detector is in any one of operational statuses of "usable", "not usable", and "alternative detector". The operational information 1301 further includes alternative detector information 1301B for identifying the first radiation detector (alternative detector) that has replaced the second radiation detector (removed detector).

<Example of Replacement Processing>

Figure 14:
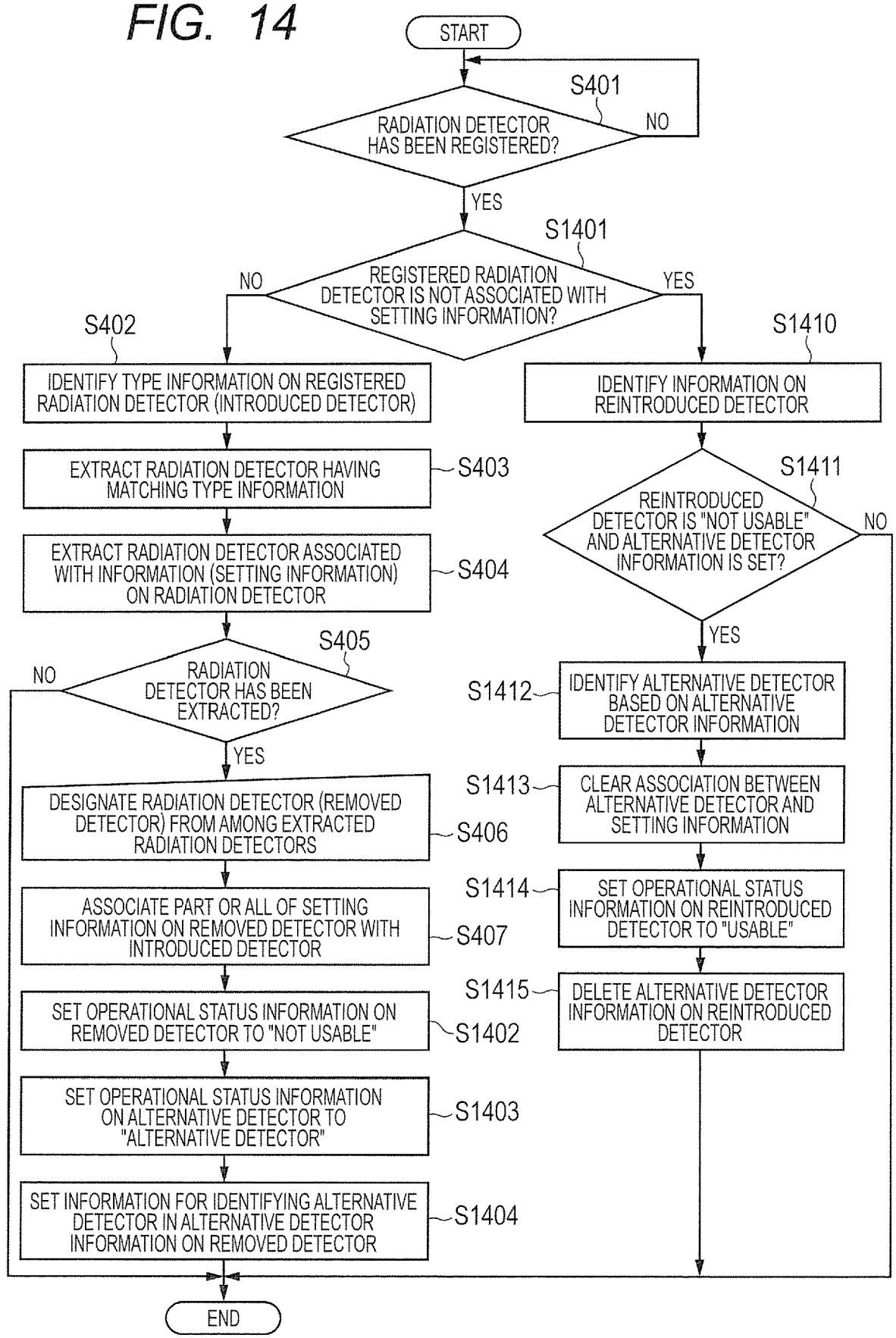
FIG. 14 is a flowchart for illustrating processing according to the fifth embodiment of the present invention.

FIG. 14 is a flowchart for illustrating an example of processing for restoring the removed detector to the status before the clearance when the information on the second radiation detector before the replacement by the alternative detector is held and the removed detector is to be reintroduced.

When the first radiation detector is registered in the radiation imaging system 100 in Step S401, the information control unit 163 determines whether or not the registered first radiation detector is associated with the setting information (Step S1401). When the alternative detector is to be newly introduced as the first radiation detector, the alternative detector is not associated with the setting information at a time of registration. Therefore, the processing advances from Step S1401 to Step S402 and the subsequent steps, and in the same manner as in the replacement processing of the first embodiment, the operational information 1301 is set while the setting information on the second radiation detector is associated with the alternative detector.

In Step S1402, the information control unit 163 sets the operational status information on the second radiation detector (removed detector) to "not usable". In Step S1403, the information control unit 163 sets the operational status information on the alternative detector registered in the radiation imaging system 100 to "alternative detector".

In Step S1404, information for identifying the alternative detector (first radiation detector) is set in the alternative detector information 1301B on the second radiation detector (removed detector). With this operation, the information on the alternative detector is associated with the second radiation detector (removed detector), which brings the alternative detector to an identifiable state, and an operation employing the alternative detector registered in the radiation imaging system 100 is enabled.

<Example of Recovery Processing and Releasing Processing>

Next, a description is made of a case of reintroducing the second radiation detector (removed detector) after being repaired. When the second radiation detector (removed detector) after being repaired is reintroduced in Step S401, the second radiation detector (reintroduced detector) is associated with the setting information at the time of registration, and hence the processing advances from Step S1401 to Step S1410 and the subsequent steps. Then, recovery processing for the second radiation detector (reintroduced detector) and removing processing for the alternative detector are conducted.

In Step S1410, the information control unit 163 identifies the information on the second radiation detector (reintroduced detector) registered in Step S401 through use of the serial number 1102A or the like. In Step S1411, the information control unit 163 determines whether or not the operational status information 1301A on the second radiation detector (reintroduced detector) is "not usable" and whether or not the alternative detector information 1301B is set for the second radiation detector (reintroduced detector).

When the operational status information 1301A is not "not usable", or when the alternative detector information 1301B is not set, it is determined that the alternative detector for the second radiation detector (reintroduced detector) has not been introduced, and the processing is brought to an end.

When it is determined in Step S1411 that the operational status information 1301A is "not usable" and that the alternative detector information 1301B is set, the processing advances to Step S1412. In Step S1412, the information control unit 163 identifies the first radiation detector (alternative detector) based on the alternative detector information 1301B. That is, the information control unit 163 identifies the first radiation detector based on the information on the alternative detector for identifying the alternative detector that has replaced the second radiation detector.

In Step S1413, the information control unit 163 removes the alternative detector from the radiation imaging system 100. In the removing processing of Step S1413, the association between the alternative detector and the setting information is cleared. That is, the information control unit 163 clears the setting information associated with the first radiation detector (alternative detector) when a part or all of the imaging setting information on the second radiation detector before the clearance is associated with the second radiation detector after the clearance.

In Step S1414, the information control unit 163 sets the operational status information 1301A on the reintroduced second radiation detector to "usable" to reset the setting information or imaging setting information before the clearance for the second radiation detector. That is, the information control unit 163 sets the second radiation detector after the clearance to "usable" based on the operational status information for managing the operational status of the radiation detector, to thereby associate the setting information or imaging setting information before the clearance with the second radiation detector after the clearance.

In Step S1415, the information control unit 163 deletes the information for identifying the alternative detector (first radiation detector) from the alternative detector information 1301B on the reintroduced second radiation detector.

With this operation, the second radiation detector (removed detector) removed from the radiation imaging system 100 is reintroduced into the radiation imaging system 100, which can bring the removed detector to a status before the clearance, and the removed detector can be operated in the same status as the status before the clearance.

According to the fifth embodiment, it is possible to reduce the workload and the operational error of the operator who associates the setting information or imaging setting information with the radiation detector when the radiation detector is to be reintroduced.

Sixth Embodiment

The first embodiment to the fifth embodiment are described by taking an example in which the replacement processing for the radiation detector is conducted in one radiation imaging system 100. A sixth embodiment of the present invention is described by taking an example in which a radiation detector shared by a plurality of radiation imaging systems exists and is replaced as the second radiation detector (removed detector).

Descriptions of the same components, functions, and operations as those of the above-mentioned embodiments are omitted, and differences between the above-mentioned embodiments and the sixth embodiment are mainly described.

The sixth embodiment assumes a case of using a radiation detector, for example, a portable wireless radiation detector, which can be easily moved and mounted to another imaging table/stand without being fixedly mounted to a specific imaging table/stand.

<Outline of Configuration of Radiation Imaging System>

Figure 15:
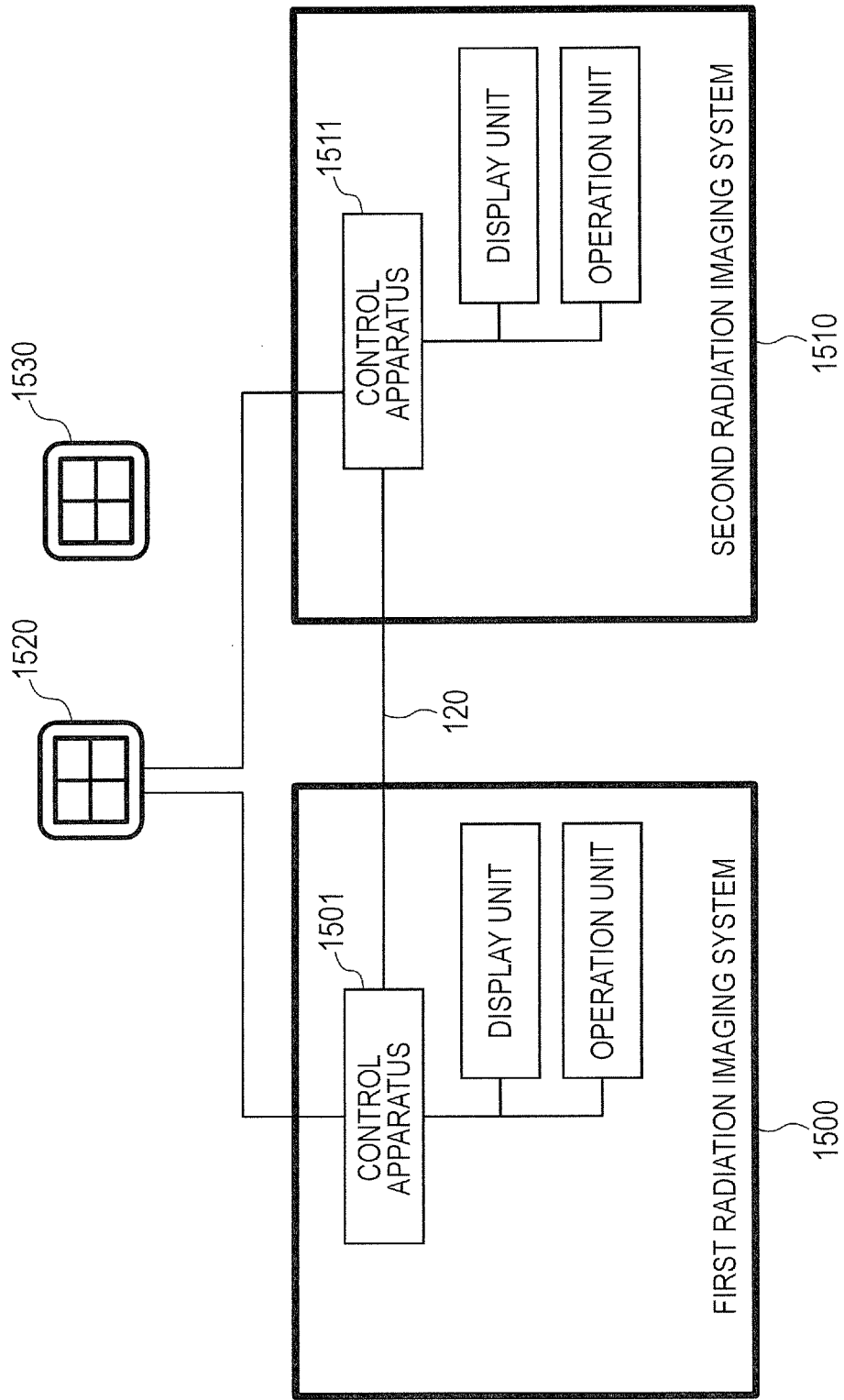
FIG. 15 is a diagram for illustrating an example of a system configuration of a plurality of radiation imaging systems according to a sixth embodiment of the present invention.

FIG. 15 is a diagram for illustrating an example of a system configuration of a plurality of radiation imaging systems for achieving the sixth embodiment. In FIG. 15, only points relating to the sixth embodiment are described, and duplicates of descriptions made with reference to FIG. are omitted. Descriptions of the same components, functions, and operations as those of the above-mentioned embodiments are omitted, and differences between the above-mentioned embodiments and the sixth embodiment are mainly described.

A first radiation imaging system 1500 and a second radiation imaging system 1510 are configured to conduct radiographic imaging through use of a radiation detector (second radiation detector) 1520 for which the setting information is set. Therefore, the information (setting information, imaging setting information, operational information, and other such information) on the radiation detector 1520 is set for a control apparatus 1501 of the first radiation imaging system 1500 and a control apparatus 1511 of the second radiation imaging system 1510. The control apparatus 1501 and 1511 can communicate to/from each other through the network 120.

Setting information on a radiation detector (introduced detector) 1530 is not set in the first radiation imaging system 1500 and the second radiation imaging system 1510, and hence the radiation detector (introduced detector) 1530 cannot be used.

<Example of Replacement Processing>

Figure 16:
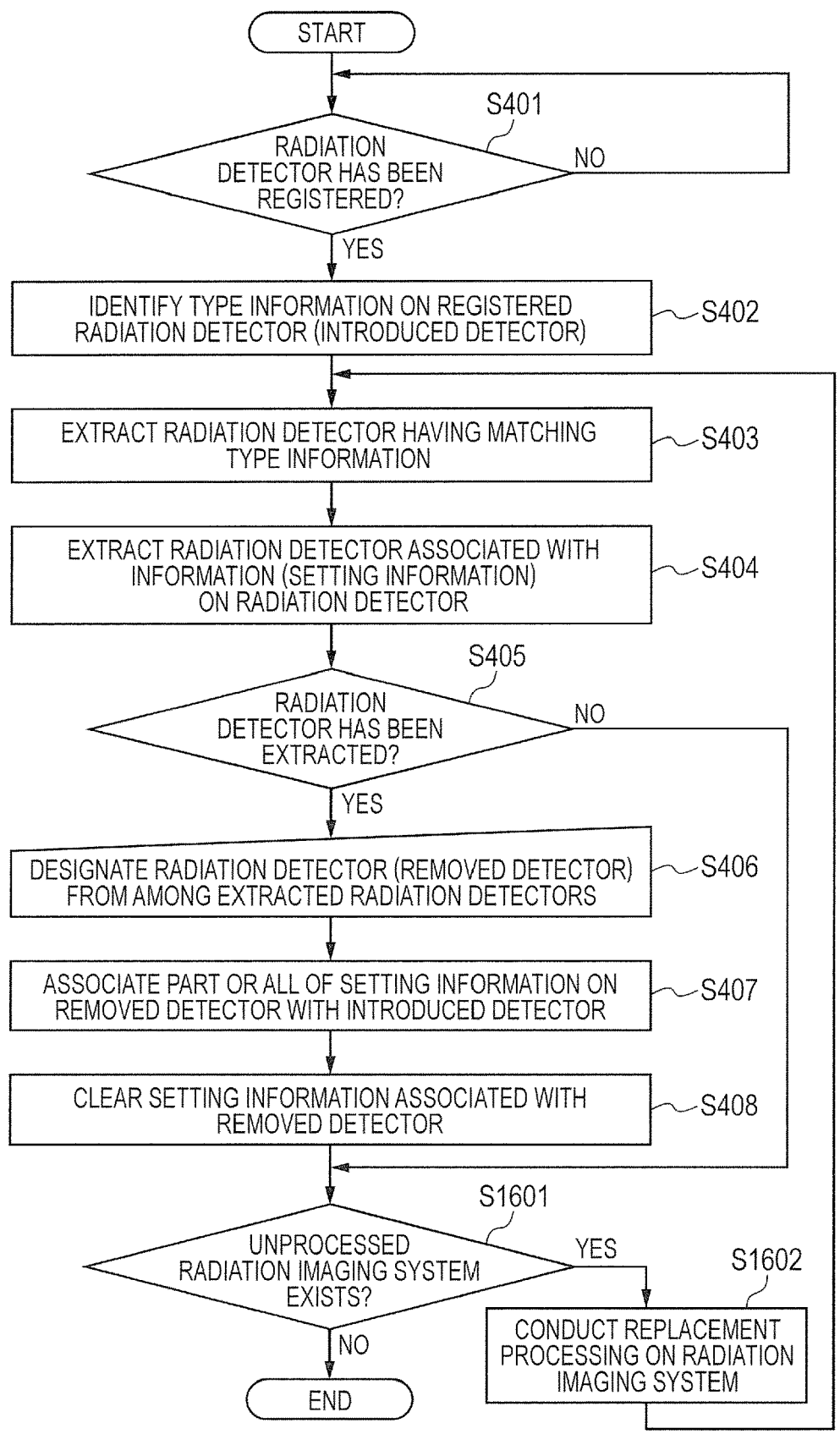
FIG. 16 is a flowchart for illustrating processing according to the sixth embodiment of the present invention.

FIG. 16 is a flowchart for illustrating an example in which the same replacement processing is also conducted in the second radiation imaging system 1510 when the replacement processing is conducted in the first radiation imaging system 1500 according to the sixth embodiment. The sixth embodiment is described with reference to FIG. 4 of the first embodiment, the descriptions of the same components, functions, and operations as those of the first embodiment are omitted, and differences between the first embodiment and the sixth embodiment are mainly described.

When the first radiation detector (introduced detector) 1530 is registered in a radiation imaging system (for example, first radiation imaging system 1500) in Step S401, the replacement processing is conducted in Step S402 and the subsequent steps. When the replacement processing is brought to an end, it is determined in Step S1601 whether or not an unprocessed radiation imaging system exists on the network 120. When the replacement processing has been conducted for all the radiation imaging systems on the network 120, the processing is brought to an end.

When there exists a radiation imaging system (for example, second radiation imaging system 1510) for which the replacement processing has not been conducted, the first radiation detector (introduced detector) 1530 registered in the radiation imaging system is designated, and the replacement processing is conducted (Step S1602).

For example, the first detector designation unit 161 designates the first radiation detector 1530 associated with the setting information in the first radiation imaging system 1500. The second detector designation unit 162 designates the second radiation detector 1520 registered in the first radiation imaging system 1500 and the second radiation imaging system 1510 and associated with the setting information on the first radiation imaging system 1500 and the second radiation imaging system 1510. The information control unit 163 executes the replacement instruction to replace the second radiation detector 1520 by the first radiation detector 1530, and associates a part or all of the setting information on the second radiation detector 1520 with the first radiation detector 1530.

The determination processing and the replacement processing are repeatedly conducted to apply the replacement processing to a plurality of radiation imaging systems on the network 120. With this operation, when the replacement processing is conducted in one radiation imaging system, the replacement processing is conducted in other radiation imaging systems on the network 120, and the first radiation detector (introduced detector) 1530 can be operated in a plurality of radiation imaging systems. The other radiation imaging systems may be selected randomly, or may be selected automatically based on a predetermined condition.

According to the sixth embodiment, it is possible to reduce the workload and the operational error of the operator who associates the setting information with the radiation detector when the radiation detector is introduced into a plurality of radiation imaging systems.

Seventh Embodiment

The radiation detector is defined as one of installation controlled medical devices under the Act on Pharmaceuticals and Medical Devices, and needs to be managed regarding whether or not the radiation detector is correctly mounted. Therefore, it may be desired to provide an authorization setting for conducting the replacement processing for the radiation detector. A seventh embodiment of the present invention is described by taking an example of providing a login screen in order to conduct the replacement processing of each of the above-mentioned embodiments. That is, the radiation imaging system 100 has a login function.

Descriptions of the same components, functions, and operations as those of the above-mentioned embodiments are omitted, and differences between the above-mentioned embodiments and the seventh embodiment are mainly described.

<Example of Login Screen>

Figure 17:
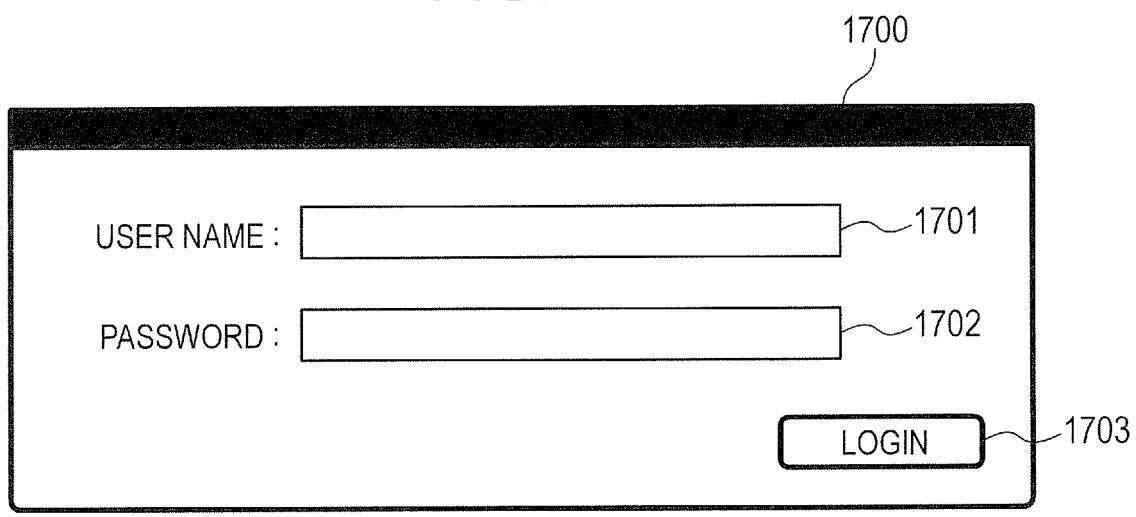
FIG. 17 is a diagram for illustrating an example of a GUI of a login screen according to a seventh embodiment of the present invention.

FIG. 17 is a diagram for illustrating an example of a login screen for achieving the seventh embodiment. A login screen 1700 includes a user name input area 1701, a password input area 1702, and a login instruction area 1703.

The user name input area 1701 is an area for designating a user name of a user who conducts the replacement processing, and includes a text box. The user name can be set in the user name input area 1701 through the operation unit 112, for example, a keyboard. The password input area 1702 is an area for designating a password corresponding to the user name designated in the user name input area 1701, and includes a text box. The password can be set through the operation unit 112, for example, a keyboard. The login instruction area 1703 is a button for instructing execution of login and start of the replacement processing.

Unless both the user name input area 1701 and the password input area 1702 are input, the button of the login instruction area 1703 is disabled. When the login instruction area 1703 is pressed and login processing is successfully conducted, a replacement information screen GUI (replacement information screen 500 or 700) illustrated in FIG. 5 or FIG. 7 is displayed. When the login processing fails, the replacement information screen GUI is not displayed, and the operator is notified that the login processing has failed.

The operator can selectively specify each button or the like through the operation unit 112. When the display unit 111 is a touch panel, the operator may selectively specify each button or the like by directly touching and operating the setting information screen 200, the setting information addition screen 300, the login screen 1700 or the like.

Other Embodiments

The embodiments of the present invention have been described above, but the present invention is not limited thereto, and changes and modifications can be made thereto within the scope of the appended claims.

When the first radiation detector (introduced detector) is to be designated, as illustrated in FIG. 18, the first detector designation unit 161 may select the first radiation detector from among a plurality of radiation detectors registered in the radiation imaging system 100. For example, the first radiation detector may be selectively designated through the checking of a checkbox 1801 within introduced detector information 1800. Time information (last update date/time or the like) on the registration may also be associated with the first radiation detector.

The introduced detector information 1800 illustrated in FIG. 18 may also be displayed on a screen without displaying introduced detector information and removed detector information on one screen unlike in FIG. 5, FIG. 7, or FIG. 10A. When a transition instruction area 1802 is pressed after the first radiation detector is designated, the screen may transition from the introduced detector information 1800 to reference detector information 1910 illustrated in FIG. 19. In the reference detector information 1910, the designated first radiation detector may be displayed, or the time information (last update date/time or the like) on the setting information set for the second radiation detector (reference detector) may be displayed.

In the same manner as in FIG. 7, the operator may also be inhibited from checking a checkbox 1912 for designating the second radiation detector when the second radiation detector has the type information that does not match the type information on the first radiation detector. Further, the display unit 111 may preferentially display the second radiation detector having the type information that matches the type information on the first radiation detector, or may avoid displaying the second radiation detector having the type information that does not match the type information on the first radiation detector. Further, when the second radiation detector having the type information that matches the type information on the first radiation detector does not exist, the operator may be notified that there exists no applicable second radiation detector with the message that "No detector can be added or replaced." or other such message.

In addition, an addition instruction part 1913 is a button for associating the setting information with the second radiation detector. When the addition instruction part 1913 is pressed, the information control unit 163 associates a part or all of the setting information on the second radiation detector (reference detector) with the first radiation detector (introduced detector). Then, in the set device list 210 on the setting information screen 200 of FIG. 2, the first radiation detector is displayed in association with the setting information on the second radiation detector (with the checkbox 210A within the first radiation detector being checked).

In this case, the information control unit 163 does not clear the setting information associated with the second radiation detector (reference detector). Therefore, the check in the checkbox 210A for the second radiation detector is not cleared.

A replacement instruction part 1914 is a button for executing the replacement instruction to replace the second radiation detector by the first radiation detector and to associate the setting information on the second radiation detector with the first radiation detector. In this case, the information control unit 163 clears the setting information associated with the second radiation detector (reference detector). Therefore, in the set device list 210 on the setting information screen 200, the second radiation detector is displayed with the association with the setting information being cleared (with the check in the checkbox 210A for the second radiation detector being cleared).

When the addition instruction part 1913 or the replacement instruction part 1914 is pressed, the setting information screen 200 is displayed. When a creation cancellation instruction is executed through a cancellation instruction part 1903, the reference detector information 1910 finishes being displayed.

Further, the information control unit 163 may also selectively associate a part of the information (setting information, imaging setting information, and operational information) on the second radiation detector with the first radiation detector. FIG. 20 and FIG. 21 are diagrams for illustrating how a part of the setting information on the second radiation detector is selectively associated with the first radiation detector.

As illustrated in FIG. 20, the second radiation detector is designated by checking the checkbox 2012 within reference detector information 2010. The setting information on the second radiation detector is designated by checking a checkbox 2020 for the setting information on the designated second radiation detector. The information control unit 163 associates the designated setting information on the second radiation detector with the first radiation detector.

As illustrated in FIG. 21, the setting information of the second radiation detector may be designated by extracting the second radiation detector which has the type information that matches the type information of the first radiation detector and checking a checkbox 2120 in reference detector information 2110. The information control unit 163 associates the designated setting information on the second radiation detector with the first radiation detector. In this case, the information control unit 163 may associate the setting information designated from a plurality of second radiation detectors with the first radiation detector.

As illustrated in FIG. 20 and FIG. 21, the operator may be inhibited from checking any one of the checkboxes 2020 and 2120 for designating the information on the second radiation detector when the second radiation detector has the type information that does not match the type information on the first radiation detector.

According to the above-mentioned embodiments of the present invention, it is possible to provide a technology capable of reducing the workload of the operator at the time of introduction of the radiation detector.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2016-132997, filed Jul. 5, 2016, which is hereby incorporated by reference herein in its entirety.

What is claimed is:

1. A radiation imaging apparatus, comprising:
   a radiation detector configured to detect radiation;
   at least one of one or more processors or circuitry configured to function as a plurality of units including:
      a first detector designation unit configured to designate a first radiation detector which is not registered in the radiation imaging apparatus;
      a second detector designation unit configured to designate a second radiation detector registered in the radiation imaging apparatus in advance; and
      an information control unit configured to associate setting information on the second radiation detector with the first radiation detector after the first radiation detector and the second radiation detector are designated,
   wherein the second detector designation unit is configured to extract radiation detectors having information relating to a type which matches information relating to a type of the first radiation detector from among radiation detectors registered in the radiation imaging apparatus and associated with the setting information in the radiation imaging apparatus, and to designate the second radiation detector from among the extracted radiation detectors.

2. A radiation imaging apparatus according to claim 1, wherein the information control unit is configured to clear the setting information associated with the second radiation detector.

3. A radiation imaging apparatus according to claim 1, wherein the setting information comprises at least one of information relating to one of an imaging table and an imaging stand mounted with the radiation detector, information relating to a type of the radiation detector, or information relating to a mounted position of the radiation detector corresponding to a posture of a subject to be examined.

4. A radiation imaging apparatus according to claim 1, wherein the first detector designation unit is configured to designate the first radiation detector when the radiation detector, which is not registered in the radiation imaging apparatus, and is not associated with the setting information in the radiation imaging apparatus, is to be registered in the radiation imaging apparatus.

5. A radiation imaging apparatus according to claim 1, wherein the first detector designation unit is configured to designate the first radiation detector based on individual information on the radiation detector.

6. A radiation imaging apparatus according to claim 1, wherein the second detector designation unit is configured to designate the second radiation detector based on individual information on the radiation detector.

7. A radiation imaging apparatus according to claim 1, wherein the information control unit is configured to give notification for indicating that the setting information is unable to be associated when there is a mismatch in information relating to a type between the first radiation detector and the second radiation detector.

8. A radiation imaging apparatus according to claim 1, wherein the information control unit is configured to associate imaging setting information relating to imaging conducted by the second radiation detector with the first radiation detector after the first radiation detector and the second radiation detector are designated.

9. A radiation imaging apparatus according to claim 8, wherein the imaging setting information comprises at least one of calibration information, imaging angle information, or communication setting information on the second radiation detector.

10. A radiation imaging apparatus according to claim 1, wherein, when the second radiation detector is reintroduced into the radiation imaging apparatus after the setting information associated with the second radiation detector is cleared, the information control unit associates the setting information on the second radiation detector before the clearance with the reintroduced second radiation detector.

11. A radiation imaging apparatus according to claim 8, wherein, when the second radiation detector is reintroduced into the radiation imaging apparatus after the setting information associated with the second radiation detector is cleared, the information control unit associates the imaging setting information on the second radiation detector before the clearance with the reintroduced second radiation detector.

12. A radiation imaging apparatus according to claim 1, wherein the second detector designation unit extracts the second radiation detector, which is registered in the radiation imaging apparatus in advance, and has the same type as a type of the first radiation detector.

13. A radiation imaging system, comprising:
a radiation generator configured to generate radiation;
a radiation detector configured to detect the radiation;
at least one of one or more processors or circuitry configured to function as a plurality of units including:
  a first detector designation unit configured to designate a first radiation detector, which is not registered as in a radiation imaging apparatus;
  a second detector designation unit configured to designate a second radiation detector registered in the radiation imaging system in advance; and
  an information control unit configured to associate setting information on the second radiation detector with the first radiation detector after the first radiation detector and the second radiation detector are designated,
wherein the second detector designation unit is configured to extract the radiation detector having information relating to a type which matches information relating to a type of the first radiation detector from among the radiation detectors registered in the radiation imaging apparatus and associated with the setting information in the radiation imaging apparatus, and to designate the second radiation detector from among the extracted radiation detectors.

14. A radiation imaging method, comprising:
designating a first radiation detector, which is not registered in a radiation imaging apparatus, to be introduced into a radiation imaging system;
designating a second radiation detector registered in the radiation imaging system in advance;
associating setting information on the second radiation detector with the first radiation detector after the first radiation detector and the second radiation detector are designated;
extracting radiation detectors having information relating to a type which matches information relating to a type of the first radiation detector from among radiation detectors registered in the radiation imaging apparatus and associated with the setting information in the radiation imaging apparatus; and
designating the second radiation detector from among the extracted radiation detectors.

15. A non-transitory computer-readable medium having stored thereon a program to be executed by a processor to cause the processor to execute the procedures of:
designating a first radiation detector, which is not registered as in a radiation imaging apparatus, to be introduced into a radiation imaging system;
designating a second radiation detector registered in the radiation imaging system in advance;
associating setting information on the second radiation detector with the first radiation detector after the first radiation detector and the second radiation detector are designated;
extracting radiation detectors having information relating to a type which matches information relating to a type of the first radiation detector from among radiation detectors registered in the radiation imaging apparatus and associated with the setting information in the radiation imaging apparatus; and
designating the second radiation detector from among the extracted radiation detectors.

* * * * *